United States Patent
Yamada et al.

(10) Patent No.: US 10,094,760 B2
(45) Date of Patent: *Oct. 9, 2018

(54) PARTICLE MEASURING APPARATUS

(71) Applicant: Sysmex Corporation, Kobe-shi, Hyogo (JP)

(72) Inventors: Kazuhiro Yamada, Kobe (JP); Takeshi Yamamoto, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 23 days.

This patent is subject to a terminal disclaimer.

(21) Appl. No.: 15/341,687

(22) Filed: Nov. 2, 2016

(65) Prior Publication Data

US 2017/0108426 A1   Apr. 20, 2017

Related U.S. Application Data

(63) Continuation of application No. 14/227,618, filed on Mar. 27, 2014, now Pat. No. 9,513,206.

(30) Foreign Application Priority Data

Mar. 29, 2013   (JP) ................................. 2013-072987

(51) Int. Cl.
*G01N 15/14* (2006.01)
*G01N 21/53* (2006.01)
(Continued)

(52) U.S. Cl.
CPC ..... *G01N 15/1436* (2013.01); *G01N 15/1459* (2013.01); *G01N 21/53* (2013.01);
(Continued)

(58) Field of Classification Search
None
See application file for complete search history.

(56) References Cited

U.S. PATENT DOCUMENTS

| 4,498,766 A | 2/1985 | Unterleitner |
| 4,599,307 A | 7/1986 | Saunders |

(Continued)

FOREIGN PATENT DOCUMENTS

| EP | 0 950 890 A2 | 10/1999 |
| GB | 2 494 733 A | 3/2013 |

(Continued)

OTHER PUBLICATIONS

Kummrow, A. et al, "Microfluidic Structures for Flow Cytometric Analysis of Hydrodynamically Focussed Blood Cells Fabricated by Ultraprecision Micromachining", *Lab on a Chip*, vol. 9, No. 7, Jan. 5, 2009, pp. 972-981.

(Continued)

*Primary Examiner* — Jill A Warden
*Assistant Examiner* — Matthew D Krcha
(74) *Attorney, Agent, or Firm* — Brinks Gilson and Lione

(57) ABSTRACT

A particle measuring apparatus includes a flow cell configured to flow a specimen, a first light source configured to emit light having a first wavelength, and a second light source configured to emit light having a second wavelength different from the first wavelength. An irradiation optical system is configured to irradiate the flow cell with light emitted from the first light source and the second light source. The irradiation optical system includes a dichroic mirror configured to transmit the light emitted from the first light source and reflect the light emitted from the second light source, and a light collecting lens configured to collect the light emitted from the first and second light sources and passed through the dichroic mirror at the flow cell. The second light source and the dichroic mirror are turnable about rotation axis that are orthogonal to one another.

18 Claims, 19 Drawing Sheets

(51) Int. Cl.
*G01N 15/00* (2006.01)
*G01N 15/10* (2006.01)

(52) U.S. Cl.
CPC ........ *G01N 2015/0065* (2013.01); *G01N 2015/1006* (2013.01); *G01N 2201/068* (2013.01)

(56) References Cited

U.S. PATENT DOCUMENTS

| | | |
|---|---|---|
| 4,732,479 A | 3/1988 | Tanaka et al. |
| 4,957,363 A | 9/1990 | Takeda et al. |
| 4,999,513 A | 3/1991 | Ito et al. |
| 5,426,499 A | 6/1995 | Kosaka et al. |
| 5,694,257 A * | 12/1997 | Arnone ............... G02B 7/004 359/822 |
| 5,737,078 A | 4/1998 | Takarada et al. |
| 5,760,900 A | 6/1998 | Ito et al. |
| 2005/0105077 A1 | 5/2005 | Padmanabhan et al. |
| 2005/0213202 A1* | 9/2005 | Hoffmann ............. B82Y 15/00 359/368 |
| 2007/0239380 A1 | 10/2007 | Miles |
| 2009/0122311 A1 | 5/2009 | Kanda |
| 2009/0174811 A1* | 7/2009 | Sung .................. H04N 1/6058 348/396.1 |
| 2009/0174881 A1 | 7/2009 | Rich |
| 2010/0327184 A1* | 12/2010 | Hayashi ............. G01N 15/1436 250/459.1 |
| 2011/0256523 A1 | 10/2011 | Mendele et al. |
| 2012/0051518 A1 | 3/2012 | Omote et al. |

FOREIGN PATENT DOCUMENTS

| | | |
|---|---|---|
| JP | 02-304332 A | 12/1990 |
| JP | 08-082588 A | 3/1996 |
| JP | 2000-046723 A | 2/2000 |
| JP | 2005-164304 A | 6/2005 |
| JP | 2012-247529 A | 12/2012 |
| WO | WO 02/101339 A2 | 12/2002 |
| WO | WO 2013/013228 A1 | 1/2013 |

OTHER PUBLICATIONS

Otten, Gillis R. et al., "Two Color Light Scattering Identifies Physical Differences Between Lymphocyte Subpopulations", *Cytometry*, vol. 3, No. 3, 1982, pp. 182-187.

Zucker, Robert M. et al., "Utility of Light Scatter in the Morphological Analysis of Sperm", *Cytometry*, Wiley-Liss, Inc., New York, US., vol. 13, 1992, pp. 39-47.

James V. Waton, "Dual Laser Beam Focussing for Flow Cytometry Though a Single Crossed Cylindrical Lens Pair", *Cytometry*, vol. 1, No. 1981, 1981, pp. 14-19.

* cited by examiner

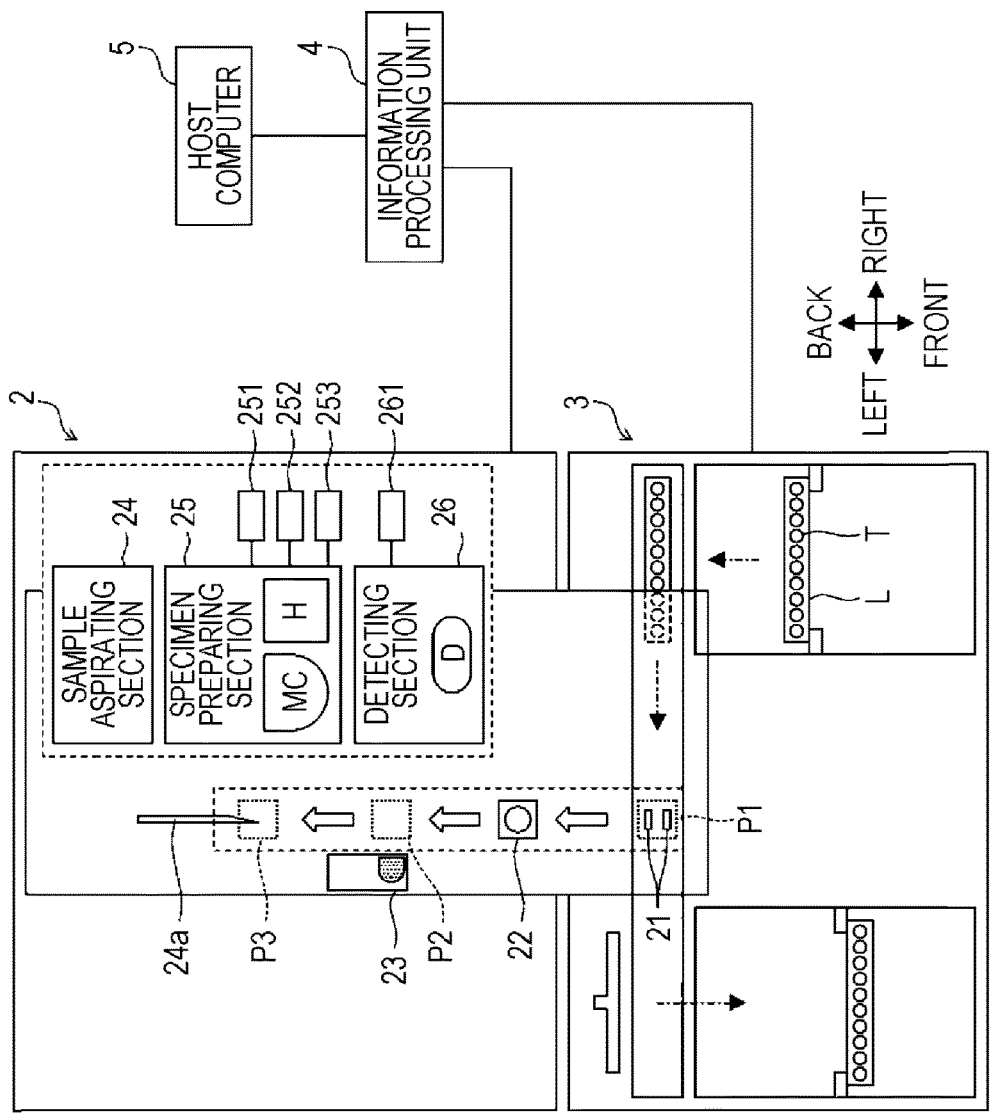

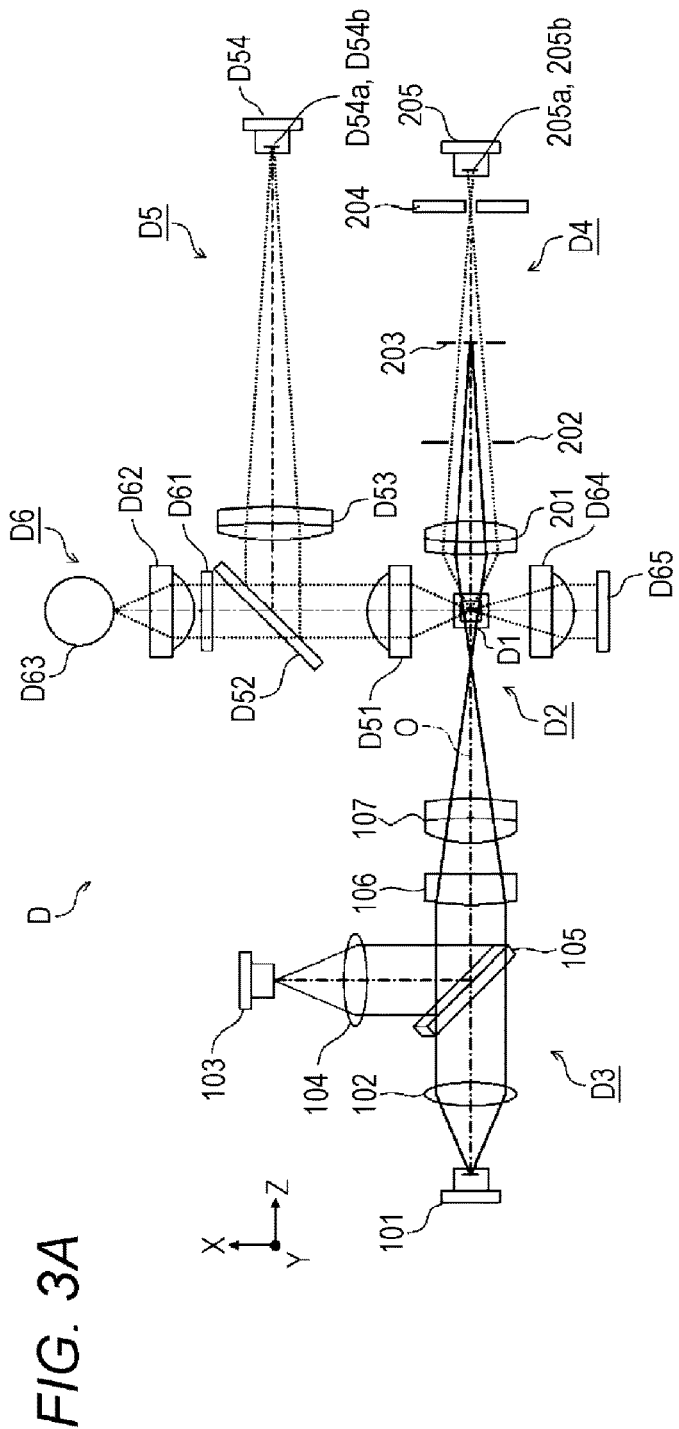
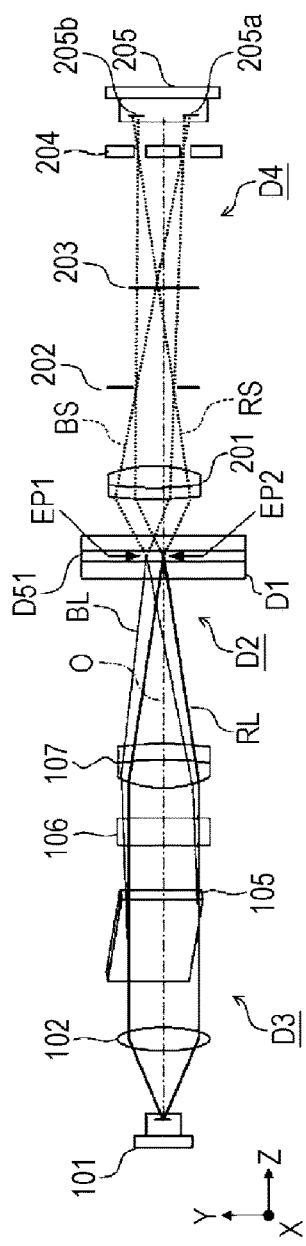
FIG. 3A
FIG. 3B

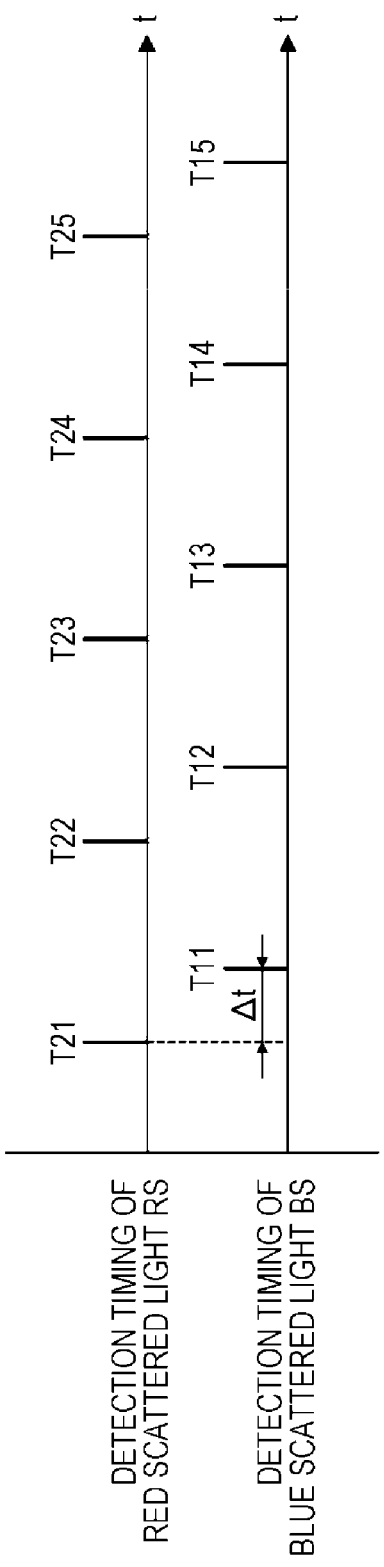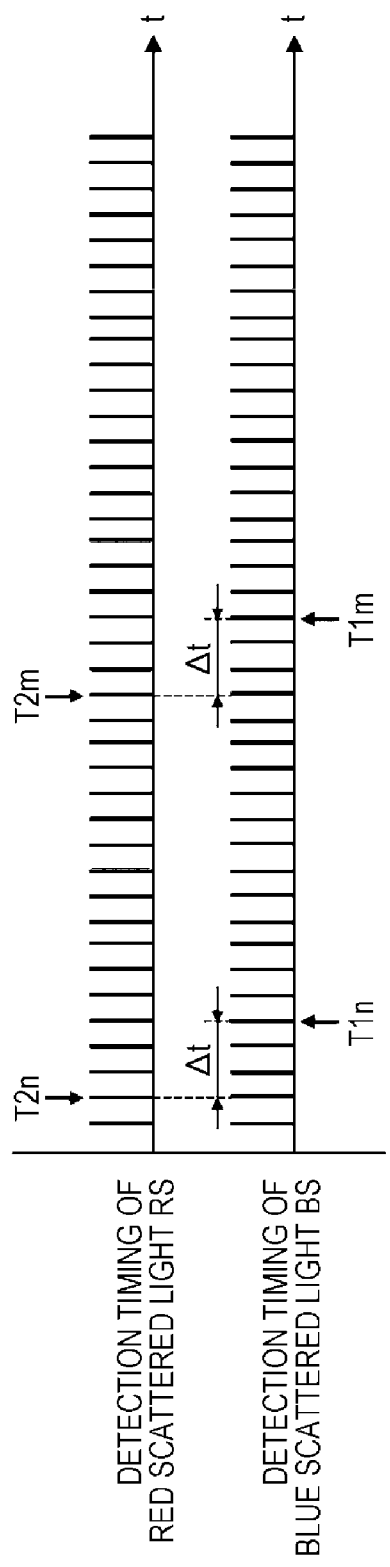

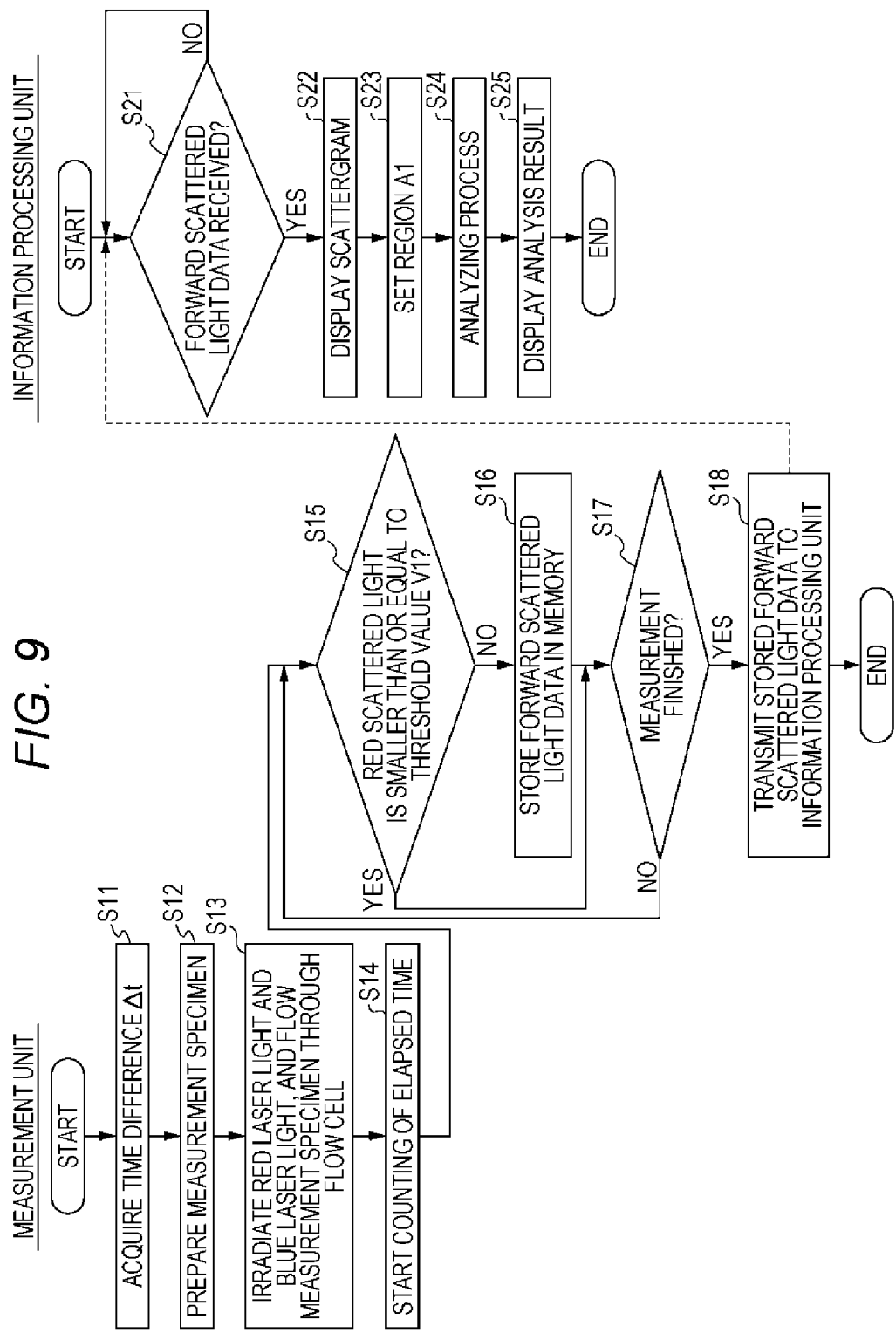

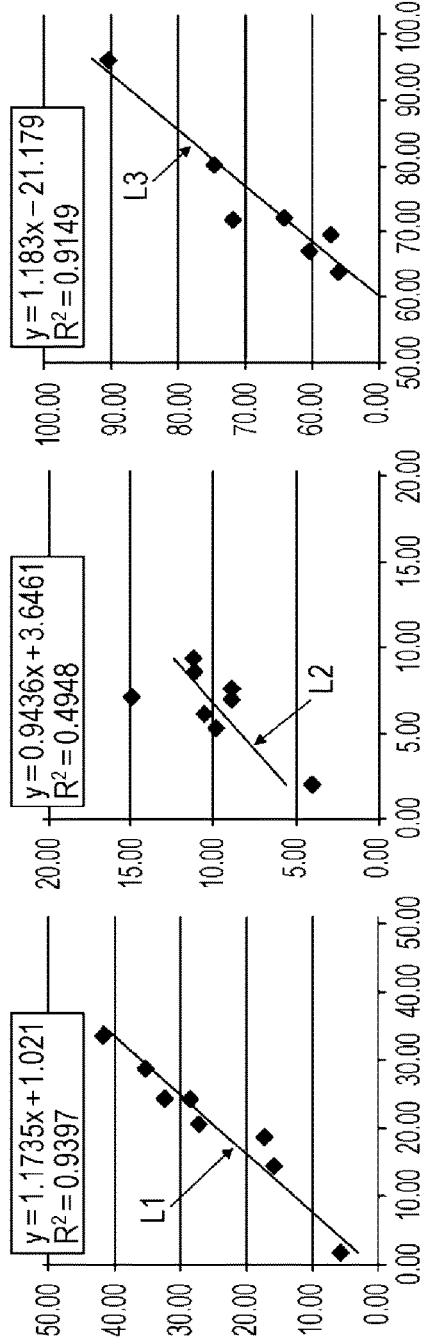

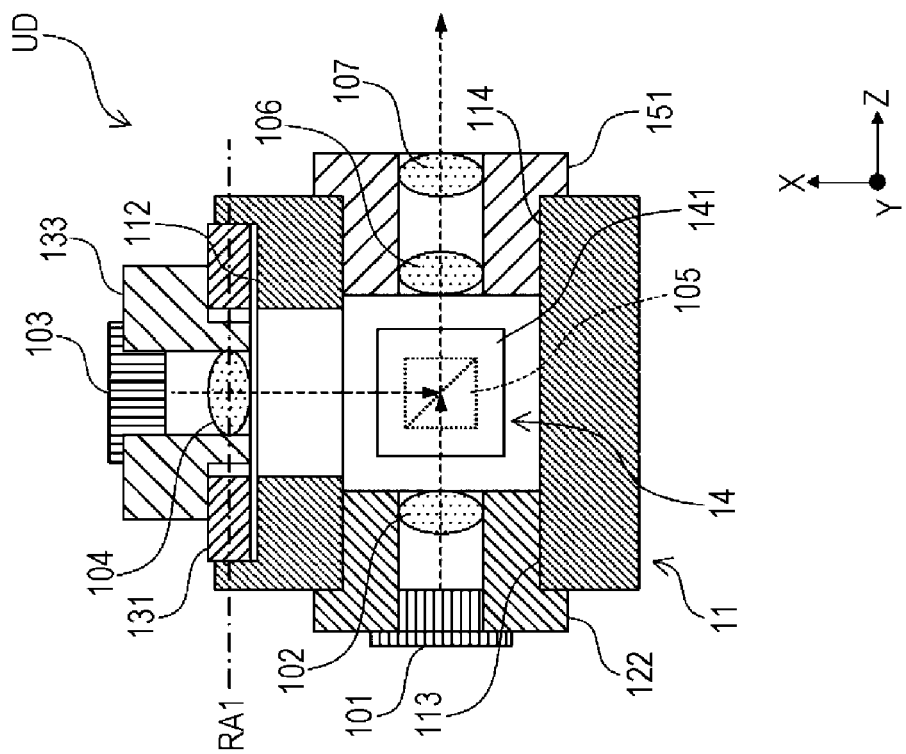
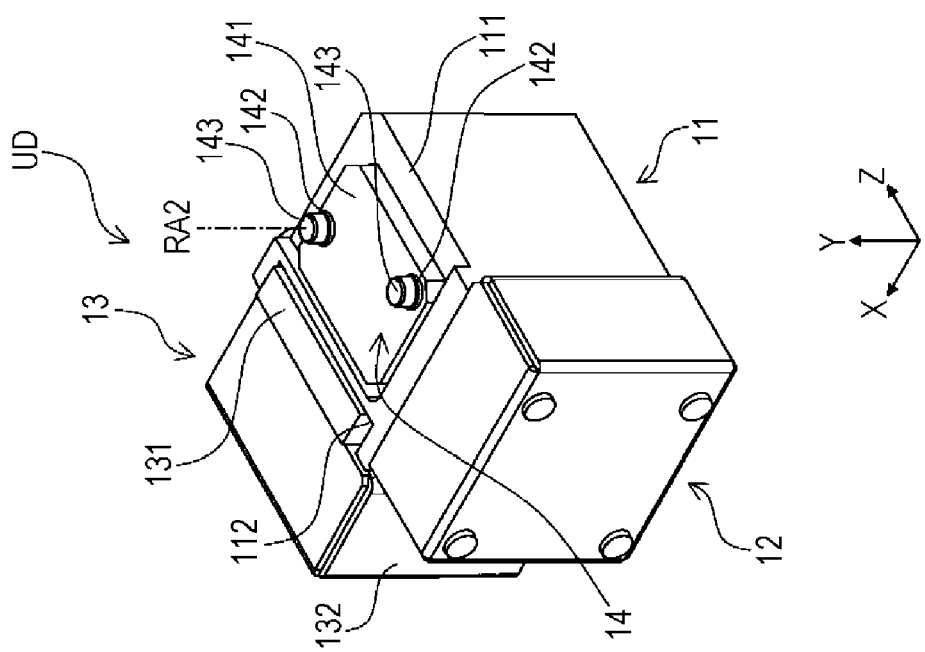

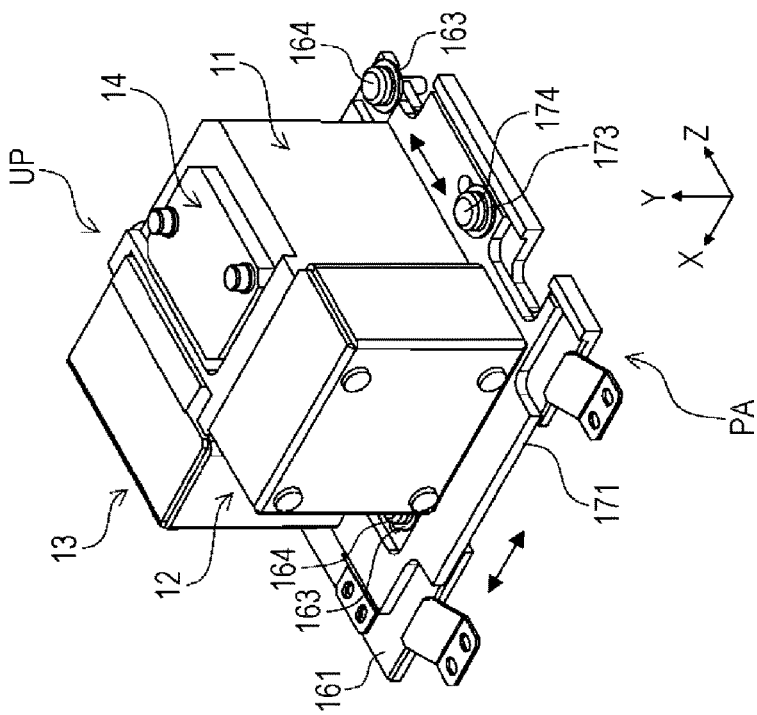
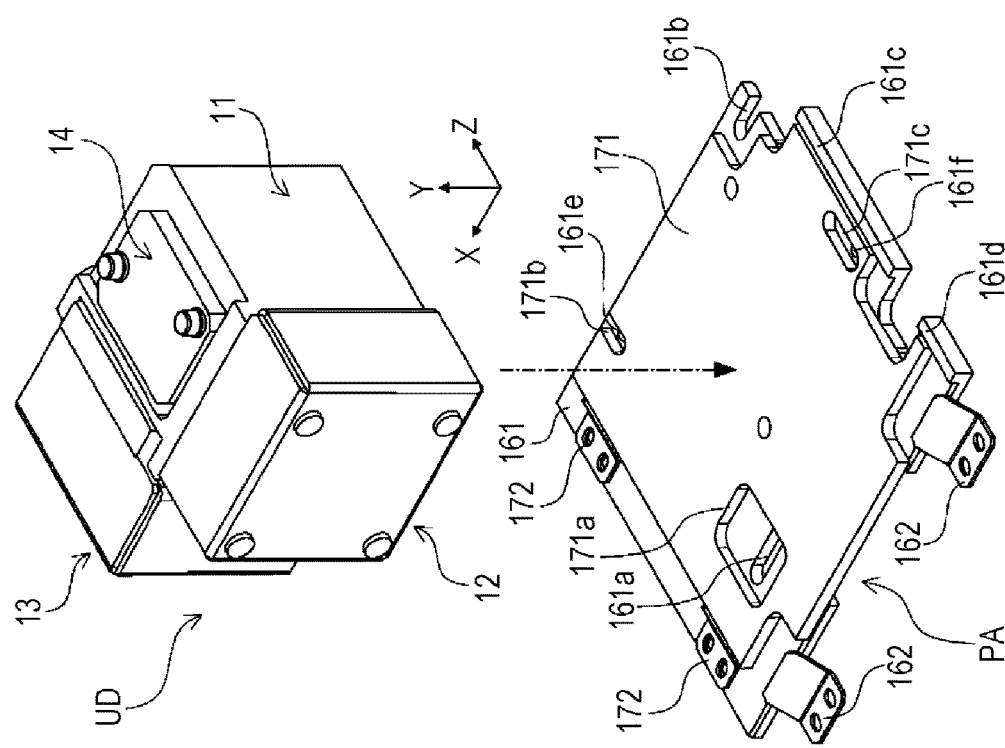

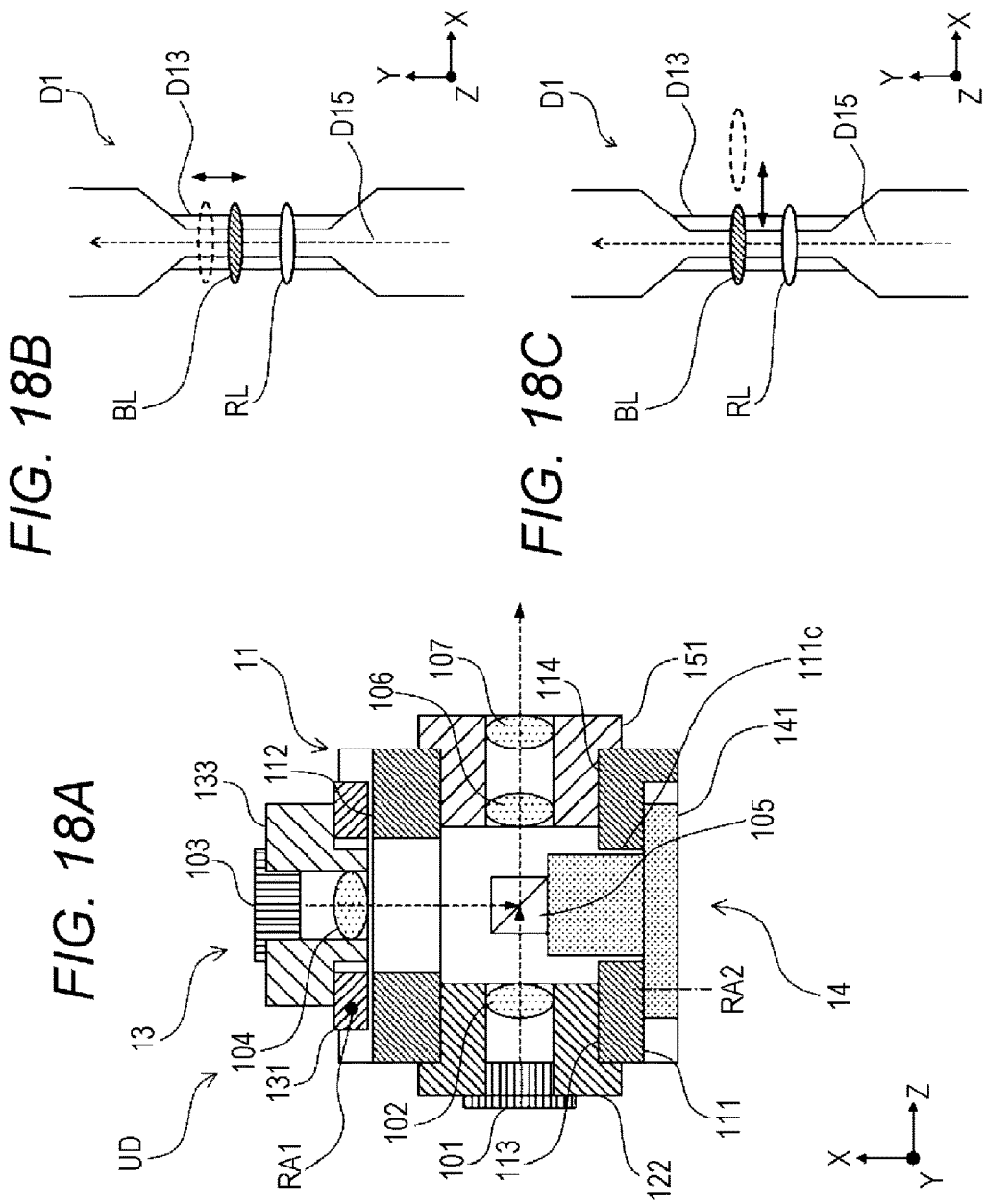

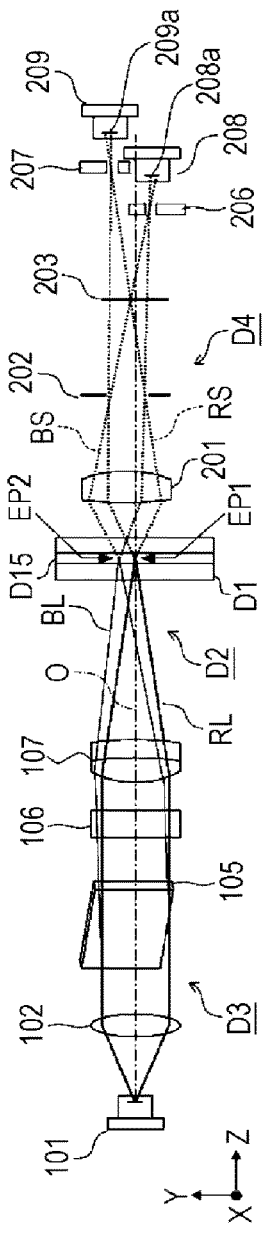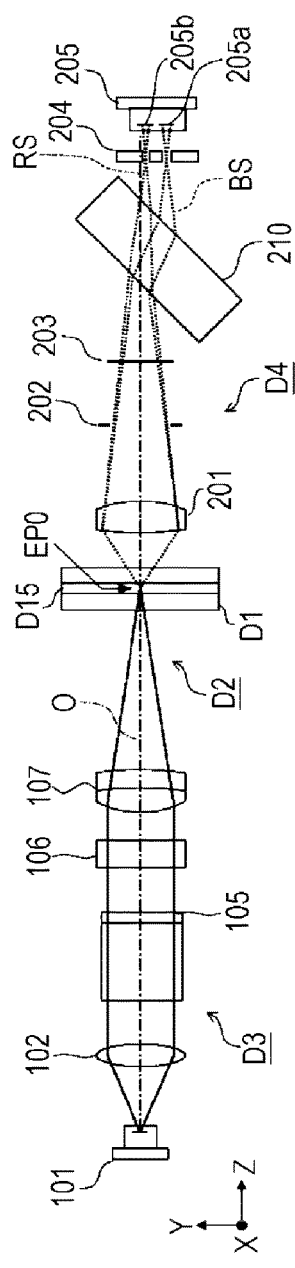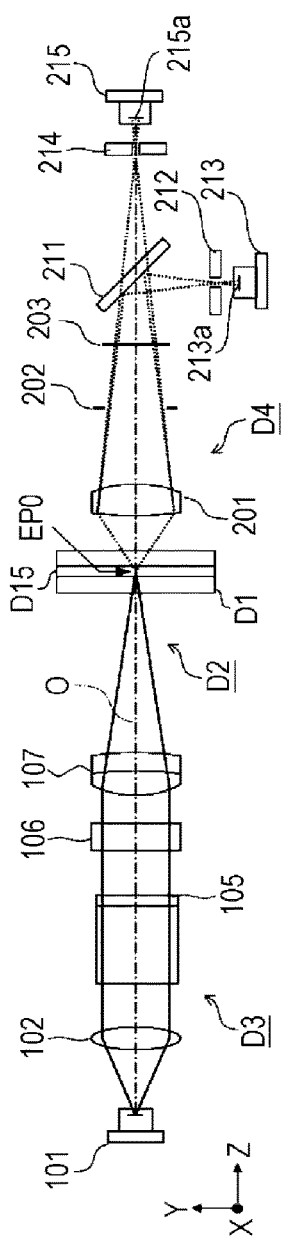
FIG. 19A
FIG. 19B
FIG. 19C

PARTICLE MEASURING APPARATUS

RELATED APPLICATIONS

This application is a continuation application of U.S. patent application Ser. No. 14/227,618, filed Mar. 27, 2014, which claims priority under 35 U.S.C. § 119 to Japanese Patent Application No. 2013-072987 filed on Mar. 29, 2013, the entire content of which is hereby incorporated by reference.

TECHNICAL FIELD

The present invention relates to a particle measuring apparatus for measuring particles by irradiating a flow including particles such as blood cells with light.

BACKGROUND

A particle measuring apparatus using an optical flow cytometer is conventionally known. In this type of particle measuring apparatus, a specimen containing testing particles such as blood, and the like, is flowed through a flow cell, and the flow path is irradiated with the light emitted from a light source. The light emitted from each particle is detected by a light receiving optical system, and the particles are classified and counted based on the detected light.

US Patent Application Publication No. 2009/122311A describes a particle measuring apparatus that irradiates a specimen containing stained cells with a plurality of laser lights having different wavelengths, and acquires fluorescence excited and generated from the respective laser lights.

However, in the particle measuring apparatus of US Patent Application Publication No. 2009/122311A, a band pass filter that selectively transmits the blue laser beam is used in a forward scattered light detection device, and a band pass filter BPF1 that transmits only the blue side scattered light is also used with respect to a photomultiplier tube PMT1 for detecting the side scattered light. Thus, only the scattered light generated when the blue laser beam is scattered by cells is used for the scattered light when analyzing the particles.

SUMMARY

The scope of the present invention is defined solely by the appended claims, and is not affected to any degree by the statements within this summary.

In a first aspect, a particle measuring apparatus includes a flow cell configured to flow a specimen, a first light source configured to emit light having a first wavelength, and a second light source configured to emit light having a second wavelength different from the first wavelength. An irradiation optical system is configured to irradiate the flow cell with light emitted from the first light source and the second light source. The irradiation optical system includes a dichroic mirror configured to transmit the light emitted from the first light source and reflect the light emitted from the second light source, and a light collecting lens configured to collect the light emitted from the first and second sources and passed through the dichroic mirror at the flow cell. The second light source and the dichroic mirror are turnable about rotation axis that are orthogonal to one another.

A second aspect of the present invention is a particle measuring apparatus comprising a flow cell configured to flow a specimen, a first light source configured to emit light having a first wavelength, a second light source configured to emit light having a second wavelength different from the first wavelength, an irradiation optical system configured to irradiate the flow cell with light emitted from the first light source and the second light source, a first light receiving portion configured to receive scattered light obtained by irradiating a measurement particle passing through the flow cell with light from the first light source, and a second light receiving portion configured to receive scattered light obtained by irradiating a measurement particle passing through the flow cell with light from the second light source.

A third aspect of the present invention is a particle measuring apparatus comprising a flow cell configured to flow a specimen, a first light source configured to emit light having a first wavelength, a second light source configured to emit light having a second wavelength different from the first wavelength, an irradiation optical system configured to irradiate the flow cell with light emitted from the first light source and the second light source, a first light receiving portion configured to receive light obtained by irradiating a measurement particle passing through the flow cell with light from the first light source, a second light receiving portion configured to receive light obtained by irradiating the measurement particle passing through the flow cell with light from the second light source, and a base attached with the first light source, the second light source, and the irradiation optical system. The irradiation optical system comprises a dichroic mirror configured to transmit light emitted from the first light source and reflect light emitted from the second light source, and a light collecting lens configured to collect light emitted from the first and second light sources and passed through the dichroic mirror at the flow cell. The second light source is turnably attached to the base. The dichroic mirror is attached to the base so as to be turnable in a direction different from a turning direction of the second light source. A light collecting position of the light emitted from the second light source is displaced in either one direction of a first direction that is parallel to the flow path of the flow cell and a second direction that traverses the flow path when the second light source is turned with respect to the base, and the light collecting position of the light emitted from the second light source is displaced in the other direction of the first and second directions when the dichroic mirror is turned with respect to the base.

BRIEF DESCRIPTION OF THE DRAWING

FIG. 2 is a view schematically showing a configuration of a measurement unit according to the embodiment;

FIG. 3A is a view schematically showing an optical system configuration of an optical detector according to the embodiment, and FIG. 3B is a view of the optical system of the light detector seen from a positive direction of an X-axis;

FIGS. 7A and 7B are views describing a method of associating the data of each wavelength acquired from the same blood cell according to a first analyzing example, where FIG. 7A is a timing chart showing a timing at which a red scattered light RS and a blue scattered light BS are detected when the particle concentration is low, and FIG. 7B is a timing chart showing a timing at which the red scattered light RS and the blue scattered light BS are detected when the particle concentration is high (when the blood specimen of normal concentration is used);

FIG. 9 is a flowchart showing an analyzing process by the blood cell analyzer according to the first analyzing example;

FIGS. 10A to 10C are views showing scattergrams created based on the blood samples collected from different subjects according to a second analyzing example, respectively, and FIGS. 10D to 10F are views showing results of classification of the white blood cells carried out based on the blood samples collected from different subjects according to the second analyzing example;

FIG. 14A is a perspective view showing a light irradiation unit after assembly according to the present embodiment, and FIG. 14B is a view schematically showing a main configuration of the light irradiation unit after the assembly according to the present embodiment;

FIG. 15A is a perspective view showing a state before the light irradiation unit according to the present embodiment is installed in a position adjustment mechanism, and FIG. 15B is a perspective view showing a state in which the light irradiation unit according to the present embodiment is installed in the position adjustment mechanism;

FIG. 18A is a view schematically showing a main configuration of the light irradiation unit after the assembly according to a variant, and FIGS. 18B and 18C are views showing the position adjustment method in the Y-axis direction and the X-axis direction of the blue laser light in the light irradiation unit according to the variant; and FIGS. 19A to 19C are views schematically showing a configuration of an optical detector according to the variant.

DETAILED DESCRIPTION OF THE PREFERRED EMBODIMENTS

In the present embodiment, the present invention is applied to a blood cell analyzer and a light irradiation optical system thereof for performing examinations and analyses associated with blood. The blood cell analyzer according to the present embodiment will be described with reference to the drawings.

Figure 1:
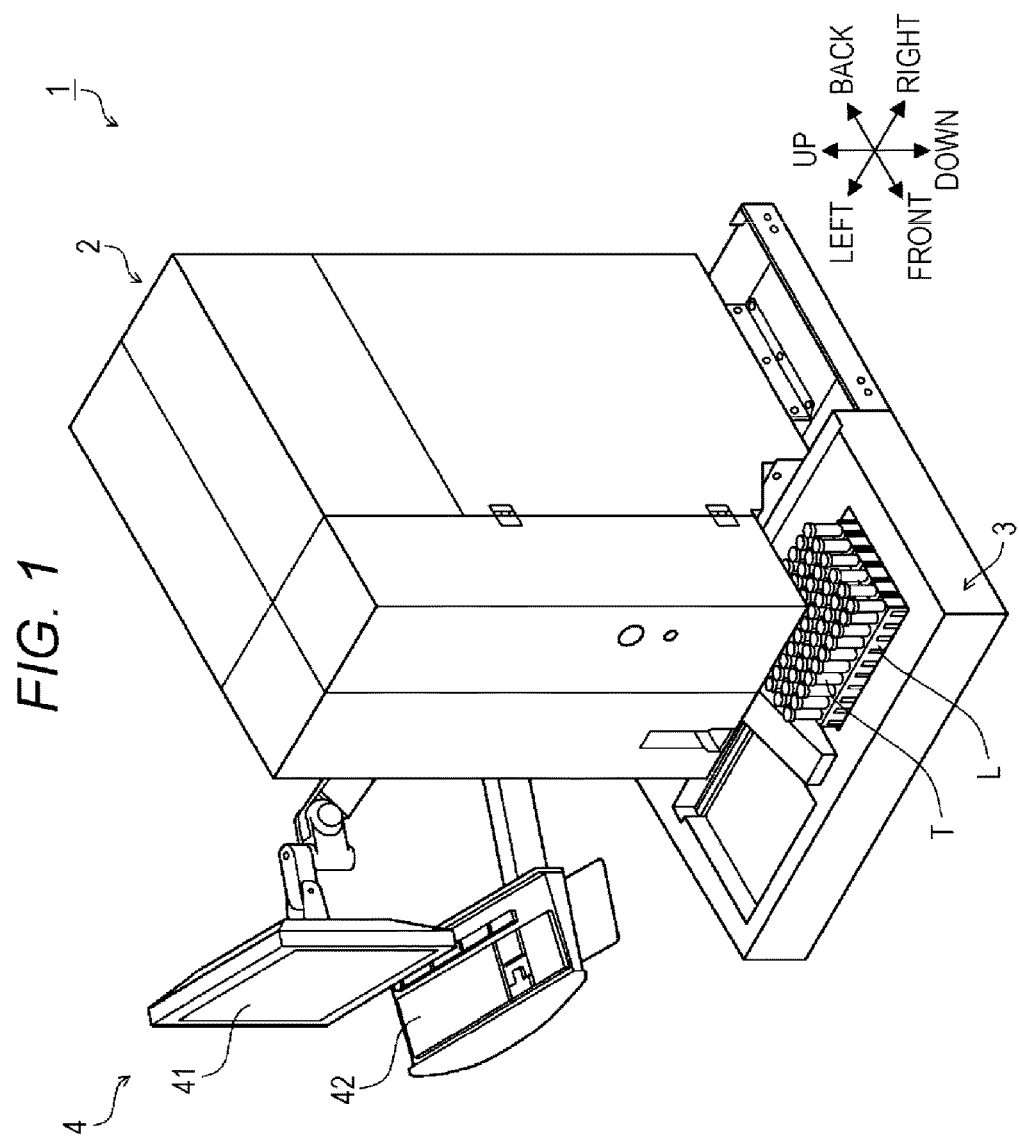
FIG. 1 is a perspective view showing an outer appearance of a blood cell analyzer according to an embodiment.

FIG. 1 is a perspective view showing an outer appearance of a blood cell analyzer 1 according to the present embodiment.

The blood cell analyzer 1 is a multiple blood cell analyzer configured to detect white blood cells, red blood cells, blood platelets, and the like contained in a blood sample, and to count each of the blood cells. The blood cell analyzer 1 includes a measurement unit 2, a transportation unit 3 arranged on a front side of the measurement unit 2, and an information processing unit 4. The blood sample, which is a peripheral blood collected from a patient, is accommodated in a sample container (blood collection tube) T. A plurality of sample containers T is supported in a sample rack L, which sample rack L is transported by the transportation unit 3 and the blood sample is supplied to the measurement unit 2.

The information processing unit 4 includes a display section 41 and an input section 42, and is communicably connected to the measurement unit 2, the transportation unit 3, and a host computer 5 (see FIG. 2). The information processing unit 4 controls the operation of the measurement unit 2 and the transportation unit 3, and performs analysis based on the measurement result of the measurement unit 2, and transmits the analysis result to the host computer 5 (see FIG. 2). The information processing unit 4 includes a personal computer.

FIG. 2 is a view schematically showing a configuration of the measurement unit 2.

The measurement unit 2 includes a hand section 21, a sample container setting section 22, a barcode unit 23, a sample aspirating section 24, a specimen preparing section 25, and a detecting section 26. The sample aspirating section 24 includes a piazza 24a, and aspirates a sample from the sample container T. The specimen preparing section 25 includes a mixing chamber MC and a heater H, and prepares a measurement specimen to be used for measurement by mixing a reagent or a diluted solution to the sample. The detecting section 26 includes an optical detector D, and detects the blood cells from the measurement specimen. Each section of the measurement unit 2 is controlled based on an instruction from the information processing unit 4.

The sample container T positioned at a position P1 by the transportation unit 3 is gripped by the hand section 21 and extracted upward from the sample rack L. The sample in the sample container T is stirred by oscillating the hand section 21. The sample container T completed with stirring is set in the sample container setting section 22 positioned at the position P1 by the hand section 21. Thereafter, the sample container T is transported to a position P2 by the sample container setting section 22.

When the sample container T is positioned at the position P2, a sample number is read from a barcode label attached to the sample container T with the barcode unit 23 installed near the position P2. Thereafter, the sample container T is transported to a position P3 by the sample container setting section 22. When the sample container T is positioned at the position P3, a predetermined amount of sample is aspirated from the sample container T through the piazza 24a by the sample aspirating section 24. After the aspiration of the sample is completed, the sample container T is transported toward the front side by the sample container setting section 22 and returned to a supporting position of the original sample rack L by the hand section 21. After the piazza 24a is transferred to the position of the mixing chamber MC, the sample aspirated through the piazza 24a is discharged by a predetermined amount to the mixing chamber MC by the sample aspirating section 24.

The specimen preparing section 25 is connected to a container 251 containing a first reagent, a container 252 containing a second reagent, and a container 253 containing a diluted solution by way of a tube. The specimen preparing section 25 is connected to a compressor (not shown), so that the first reagent, the second reagent, and the diluted solution can be aliquoted from the containers 251 to 253 with the pressure generated by the compressor. When using the first reagent and the second reagent, the specimen preparing section 25 mixes the blood sample and the reagent in the mixing chamber MC and heats the mixed solution with the heater H for a predetermined time to prepare a measurement specimen. When not using the first reagent and the second reagent, the specimen preparing section 25 mixes the blood sample and the diluted solution in the mixing chamber MC to prepare the measurement specimen. The mixed solution may be appropriately warmed even when the first reagent and the second reagent are not used. The measurement specimen prepared by the specimen preparing section 25 is supplied to the optical detector D of the detecting section 26.

The first reagent contains fluorescent pigment that can stain nucleic acid, and is a reagent for fluorescent staining the nucleic acid of the nucleated cell in the blood specimen processed with the second reagent. The second reagent is a reagent that hemolyzes the red blood cells and damages the cell membrane of the white blood cells to an extent the fluorescent pigment can be transmitted.

The detecting section 26 is connected to the container 261 containing sheath liquid by way of a tube. The detecting section 26 is also connected to a compressor (not shown), and the sheath liquid can be aliquoted from the container 261 with the pressure generated by the compressor.

FIGS. 3A and 3B are views schematically showing a configuration of an optical system of the optical detector D. FIG. 3A shows XYZ coordinate axes orthogonal to each other, for the sake of convenience. The X-axis direction is the up and down direction in the plane of drawing, and the Z-axis direction is the left and right direction in the plane of drawing. FIG. 3A is a view of the optical system of the optical detector D seen from a negative direction of the Y-axis, and FIG. 3B is a view of the optical system of the optical detector D seen from a positive direction of the X-axis.

Figure 4A:
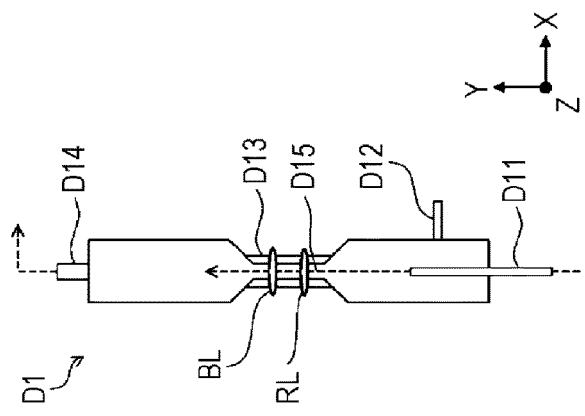
FIGS. 4A to 4D are views showing a configuration of a flow cell, a beam stopper, a pin hole, and a photodiode according to the embodiment.
Figure 4B:
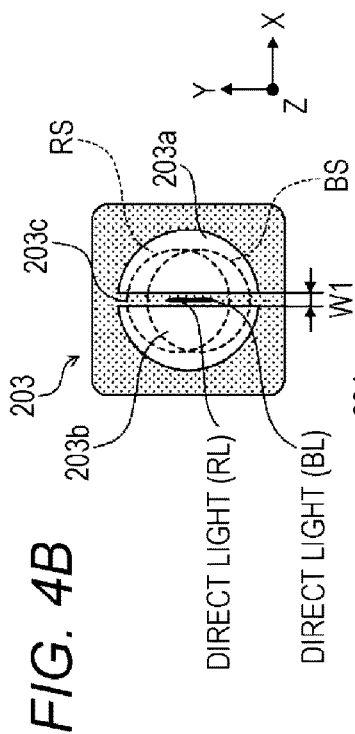
Figure 4C:
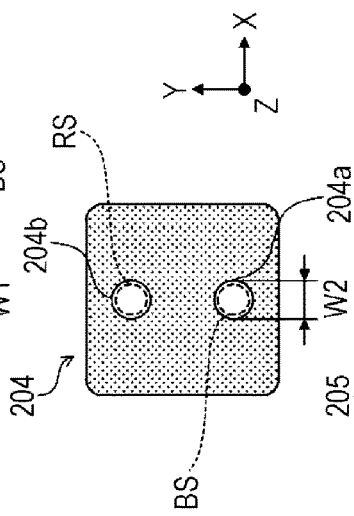
Figure 4D:
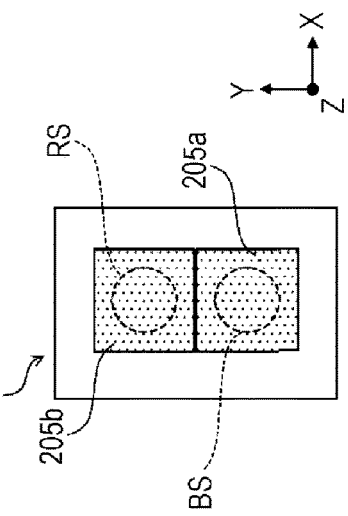

FIG. 4A is a view schematically showing a configuration of a flow cell D1, FIG. 4B is a view schematically showing a configuration of a beam stopper 203, FIG. 4C is a view schematically showing a configuration of a pin hole 204, and FIG. 4D is a view schematically showing a configuration of a photodiode 205.

With reference to FIG. 3A, the optical detector D includes the flow cell D1, a sheath flow system D2, a light irradiation optical system D3, a forward scattered light receiving optical system D4, a side scattered light receiving optical system D5, and a fluorescence light receiving optical system D6.

The sheath flow system D2 is configured to send the measurement specimen into the flow cell D1 in a state of being enveloped with the sheath liquid, and generate a liquid flow in the flow cell D1. As shown in FIG. 3B, the flow cell D1 includes a specimen nozzle D11 that ejects the measurement specimen upward toward a fine hole portion D13, a sheath liquid supply port D12, and a liquid discarding port D14. A flow path D15, through which the measurement specimen flows, is formed in the fine hole portion D13.

The light irradiation optical system D3 includes semiconductor lasers 101 and 103, collimator lenses 102 and 104, a dichroic mirror 105, a cylindrical lens 106, and a condenser lens 107.

The semiconductor laser 101 is arranged such that a stacking direction of a semiconductor layer of a light emitting portion (not shown) coincides with the X-axis direction. Therefore, a spread angle of the laser light emitted from the semiconductor laser 101 becomes a maximum in the X-axis direction, and a minimum in the Y-axis direction. The semiconductor laser 101 emits a laser light (hereinafter referred to as "red laser light RL") having a predetermined wavelength in the positive direction of the Z-axis. The emitting wavelength of the semiconductor laser 101 is set to be within a range of between 610 and 750 nm. The emitting optical axis of the semiconductor laser 101 coincides with an optical axis O of the light irradiation optical system D3.

The collimator lens 102 converts the red laser light RL emitted from the semiconductor laser 101 to a parallel light.

The semiconductor laser 103 is arranged so that a stacking direction of the semiconductor laser of the light emitting portion (not shown) coincides with the Z-axis direction. Therefore, the spread angle of the laser light emitted from the semiconductor laser 103 becomes a maximum in the Z-axis direction and a minimum in the Y-axis direction. The semiconductor laser 103 emits the laser light having a predetermined wavelength (hereinafter referred to as "blue laser light BL") in the negative direction of the X-axis. The emitting wavelength of the semiconductor laser 103 is set to be within the range of 400 and 435 nm. The emitting optical axis of the semiconductor laser 103 intersects with an optical axis O of the light irradiation optical system D3.

The collimator lens 104 converts the blue laser light BL emitted from the semiconductor laser 103 to a parallel light.

The dichroic mirror 105 transmits the red laser light RL transmitted through the collimator lens 102, and reflects the blue laser light BL transmitted through the collimator lens 104. The dichroic mirror 105 is arranged such that the advancing direction of the blue laser light BL reflected by the dichroic mirror 105 slightly tilts to the Y-axis direction from the Z-axis direction, as shown in FIG. 3B.

The cylindrical lens 106 converges the red laser light RL and the blue laser light BL passed through the dichroic mirror 105 only in the X-axis direction. The condenser lens 107 collects the red laser light RL and the blue laser light BL transmitted through the cylindrical lens 106. The condenser lens 107 converges the red laser light RL and the blue laser light BL in the Y-axis direction and focuses the same at the position of the flow path D15 (see FIG. 4A) of the flow cell D1, and furthermore, converges the red laser light RL and the blue laser light BL in the X-axis direction and focuses the same at the position in front of (negative side of the Z-axis) the flow path D15. Therefore, the light converted in the X-axis direction by the condenser lens 107 slightly spreads from the focused position to the position of the flow path D15. Thus, the flow path D15 is irradiated with the red laser light RL and the blue laser light BL in a beam shape elongated in the X-axis direction, as shown in FIG. 4A.

As shown in FIG. 3B, the blue laser light BL reflected by the dichroic mirror 105 advances in a direction slightly tilted to the Y direction from the Z-axis direction, whereby an irradiation position EP1 of the blue laser light BL with respect to the flow path D15 is shifted in the positive direction of the Y-axis than an irradiation position EP2 of the red laser light RL. The irradiation position EP2 of the red laser light RL is on the optical axis O.

The forward scattered light receiving optical system D4 includes a forward light collecting lens 201, a diaphragm 202, a beam stopper 203, a pin hole 204, and a photodiode 205. The scattered light (forward scattered light) of the red laser light RL and the blue laser light BL directed toward the front side (positive direction of the Z-axis) from the flow cell D1 are respectively collected at the position of the pin hole 204 by the forward light collecting lens 201, and thereafter, passed through the pin hole 204 and received by the photodiode 205. The photodiode 205 outputs a forward scattered light signal based on a peak value of the received forward scattered light.

The forward light collecting lens 201 is arranged such that the optical axis is shifted in the positive direction of the Y-axis from the optical axis O of the light irradiation optical system D3. Therefore, the light ray passing through the center of the forward scattered light of the red laser light RL (hereinafter referred to as "red scattered light RS") is transmitted through the forward light collecting lens 201, and then advances in a direction slightly tilted to the negative direction of the Y-axis from the positive direction of the Z-axis. The light ray passing through the center of the forward scattered light of the blue laser light BL (hereinafter referred to as "blue scattered light BS") is transmitted through the forward light collecting lens 201, and then advances in a direction slightly tilted to the positive direction of the Y-axis from the positive direction of the Z-axis.

As shown in FIG. 4C, two holes 204a and 204b lined in the Y-axis direction are formed in the pin hole 204. Each of the diameters W2 of the holes 204a and 204b is set to be slightly greater than the diameter of the converging spot of the blue scattered light BS and the red scattered light RS. The red scattered light RS is collected at the position of the hole 204b on the positive side of the Y-axis and is passed through the hole 204b. The blue scattered light BS is collected at the position of the hole 204a on the negative side of the Y-axis and is passed through the hole 204b.

As shown in FIG. 4D, two light receiving surfaces 205a and 205b lined in the Y-axis direction are arranged in the photodiode 205. The light receiving surfaces 205a and 205b are at the same position in the Z-axis direction, and are respectively parallel to the X-Y plane. The light receiving surfaces 205a and 205b are arranged on the same plane on the photodiode 205. The light receiving surface 205a is irradiated with the blue scattered light BS that passed through the hole 204a of the pin hole 204, and the light receiving surface 205b is irradiated with the red scattered light RS that passed through the hole 204b.

The magnification of the forward scattered light receiving optical system D4 is set such that the interval of the blue scattered light BS and the red scattered light RS of when irradiated on the light receiving surfaces 205a and 205b coincides with the interval of the center of the light receiving surface 205a and the center of the light receiving surface 205b. As shown in FIG. 4D, the blue scattered light BS and the red scattered light RS are respectively irradiated on the middle of the light receiving surfaces 205a and 205b.

Returning back to FIGS. 3A and 3B, the laser light (hereinafter referred to as "direct light") transmitted through the flow cell D1 without being irradiated on the particles such as the blood cells, and the like of the red laser light RL and the blue laser light BL irradiated on the flow cell D1 is collected on the beam stopper 203 by the forward light collecting lens 201. The beam stopper 203 is configured by a thin plate shaped member that does not transmit light. As shown in FIG. 4B, the beam stopper 203 includes semicircular openings 203a and 203b, and a light shielding portion 203c formed between the openings 203a and 203b. The width W1 in the X-axis direction of the light shielding portion 203c is constant. The direct light is collected on the light shielding portion 203c. As described above, the condenser lens 107 converges the laser light such that the focused position of the laser light in the X-axis direction is short of (negative side of the Z-axis) the focused position of the laser light in the Y-axis direction. Thus, the direct light is collected by the forward light collecting lens 201 such that the focused position in the X-axis direction is in front of (negative side of the Z-axis) the focused position of the Y-axis direction. The beam stopper 203 is arranged such that the incident surface is positioned at the focused position in the X-axis direction of the direct light. Therefore, the direct light is irradiated on the light shielding portion 203c in a beam shape that is long in the Y-axis direction, as shown in FIG. 4B.

In the red scattered light RS and the blue scattered light BS from the flow cell D1, the majority is passed through the openings 203a and 203b of the beam stopper 203 and one part is shielded by the light shielding portion 203c. The light shielding amount of the forward scattered light by the light shielding portion 203c is determined by the width W1 of the light shielding portion 203c. Thus, the width W1 of the light shielding portion 203c is desirably as small as possible. However, the width W1 of the light shielding portion 203c is set to about ten times the width in the X-axis direction of the direct light so that the direct light can be reliably shielded.

The side scattered light receiving optical system D5 includes a collimator lens D51, a dichroic mirror D52, a side light collecting lens D53, and a photodiode D54. The scattered light from the flow cell D1 toward the side (positive direction of the X-axis) (the side scattered light) is converted to a parallel light by the collimator lens D51. As described above, the flow cell D1 is irradiated with the red laser light RL and the blue laser light BL, and thus two side scattered lights based on each of the laser lights are generated. The collimator lens D51 converts the two side scattered lights respectively to the parallel light. The two side scattered lights converted to the parallel light are reflected by the dichroic mirror D52, and furthermore, collected by the side light collecting lens D53 and received by the photodiode D54.

The photodiode D54 includes two light receiving surfaces D54a and D54b for receiving the side scattered light of each wavelength, respectively, similar to the photodiode 205. The light receiving surfaces D54a and D54b are lined in the Y-axis direction and are at the same position in the Z-axis direction. The light receiving surfaces D54a and D54b are arranged on the same plane on the photodiode D54. The photodiode D54 outputs the side scattered light signal based on the peak value of the received side scattered light of each wavelength.

The magnification of the side scattered light receiving optical system D5 is set such that the interval of the scattered light of the blue laser light BL and the scattered light of the red laser light RL of when irradiated on the light receiving surfaces D54a and D54b coincides with the interval of the center of the light receiving surface D54a and the center of the light receiving surface D54b. The scattered lights are thereby irradiated on the middle of the light receiving surfaces D54a and D54b, respectively.

The fluorescence light receiving optical system D6 includes a light dividing filter D61, a fluorescence light collecting lens D62, an avalanche photodiode D63, a collimator lens D64, and a mirror D65. The fluorescence directed from the flow cell D1 toward the positive direction of the X-axis is converted to the parallel light by the collimator lens D51, transmitted through the dichroic mirror D52, and furthermore, passed through the light dividing filter D61, and collected by the fluorescence light collecting lens D62. The fluorescence directed from the flow cell D1 toward the negative direction of the X-axis is converted to the parallel light by the collimator lens D64, and reflected by the mirror D65. The fluorescence reflected by the mirror D65 is again passed through the collimator lens D64 and the flow cell D1 to enter the collimator lens D51. Subsequently, the fluorescence is transmitted through the dichroic mirror D52, and further passed through the light dividing filter D61, and collected by the fluorescence light collecting lens D62. The fluorescence collected by the fluorescence light collecting lens D62 is received by the avalanche photodiode D63. The avalanche photodiode D63 outputs the fluorescence signal (SFL) based on the peak value of the received fluorescence. One of the semiconductor lasers 101 and 103 is normally driven when acquiring the fluorescence signal.

In the optical system shown in FIGS. 3A and 3B, the forward light collecting lens 201 includes an achromatic lens, and has a function of correcting chromatic aberration with respect to two wavelengths of the red scattered light RS and the blue scattered light BS. Thus, the red scattered light RS and the blue scattered light BS are appropriately irradiated on the light receiving surfaces 205a and 205b arranged on the same plane. Similarly, the side light collecting lens D53 also includes an achromatic lens, and has a function of correcting the chromatic aberration with respect to the wavelengths of the two side scattered lights based on the red laser light RL and the blue laser light BL. Thus, the two side scattered lights are appropriately irradiated on the light receiving surfaces D54a and D54b arranged on the same plane.

Returning back to FIG. 2, the forward scattered light signal, the side scattered light signal, and the fluorescence signal acquired by the optical detector D are transmitted to the information processing unit 4. The information processing unit 4 executes analysis based on the received signals.

Figure 5:
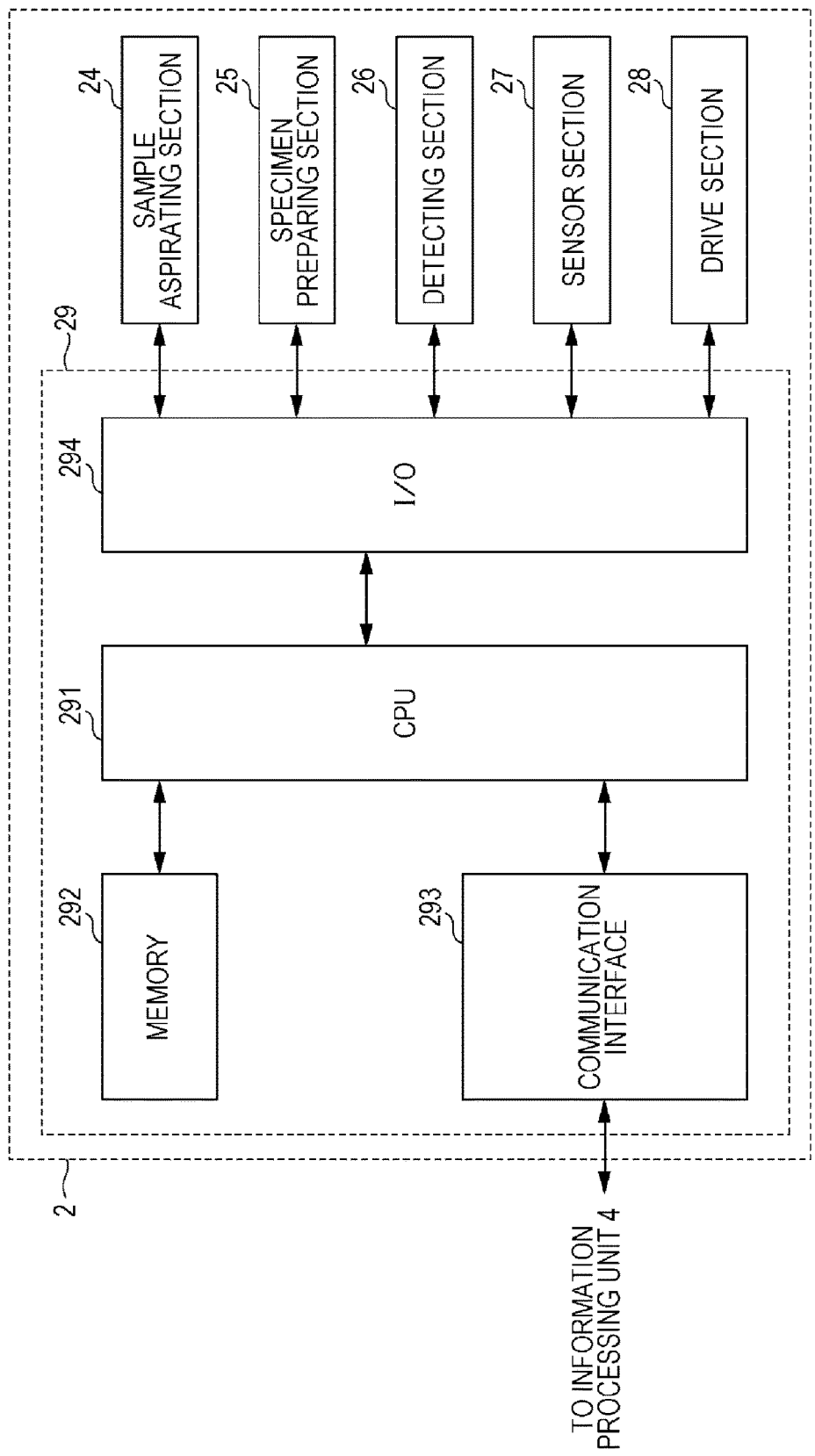
FIG. 5 is a view showing a configuration of the measurement unit according to the embodiment.

FIG. 5 is a view showing a configuration of the measurement unit 2.

The measurement unit 2 includes a sensor section 27, a drive section 28, and a control section 29 in addition to the sample aspirating section 24, the specimen preparing section 25, and the detecting section 26 shown in FIG. 2. The sensor section 27 includes a sensor, and the like for detecting the positions of the sample container T and the sample rack L, and the drive section 28 includes a mechanism for carrying out the measurement of the sample. The barcode unit 23 shown in FIG. 2 is included in the sensor section 27.

The control section 29 includes a CPU 291, a memory 292, a communication interface 293, and an I/O interface 294.

The CPU 291 executes a computer program stored in the memory 292. The memory 292 includes a ROM, a RAM, a hard disk, and the like. The CPU 291 transmits and receives data with the information processing unit 4 through the communication interface 293. The CPU 291 controls each section of the measurement unit 2 and also receives and processes the signal output from each section through the I/O interface 294. The measurement data of the blood sample obtained by the detecting section 26 is processed by the CPU 291, and stored in the memory 292. After the measurement on the blood sample is finished, the measurement data stored in the memory 292 is transmitted to the information processing unit 4 through the communication interface 293, and the analyzing process is carried out in the information processing unit 4.

Figure 6:
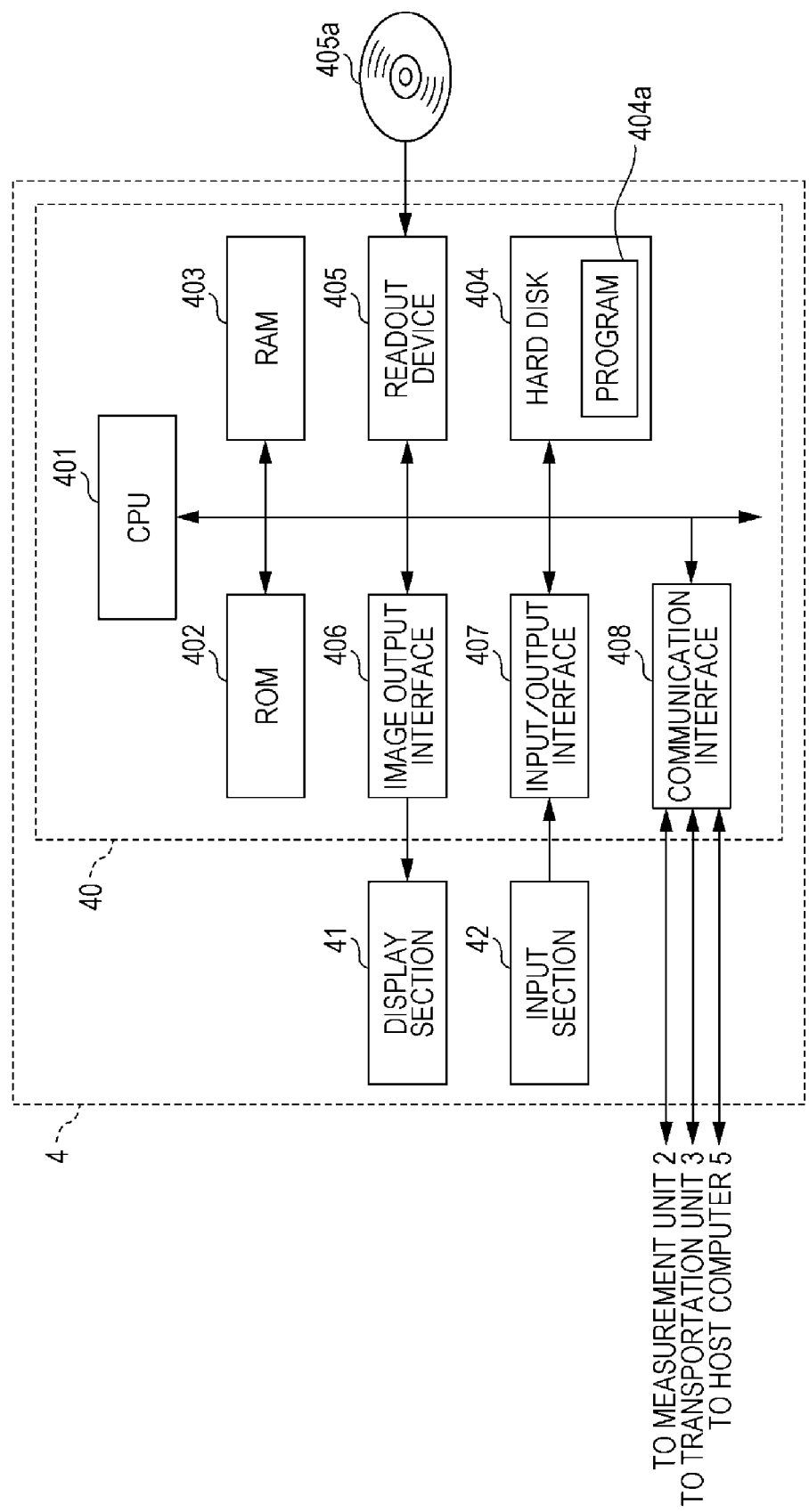
FIG. 6 is a view showing a configuration of an information processing unit according to the embodiment.

FIG. 6 is a view showing a configuration of the information processing unit 4.

The information processing unit 4 includes a personal computer, and is configured by a main body 40, a display section 41, and an input section 42. The main body 40 includes a CPU 401, a ROM 402, a RAM 403, a hard disk 404, a readout device 405, an image output interface 406, an input/output interface 407, and a communication interface 408.

The CPU 401 executes a computer program stored in the ROM 402 and a computer program loaded in the RAM 403. The RAM 403 is used to read out the computer programs recorded in the ROM 402 and the hard disk 404. The RAM 403 is also used as a work region of the CPU 401 when executing the computer programs.

The hard disk 404 is stored with an operating system, a computer program to be executed by the CPU 401, and data used in the execution of the computer program. A program 404a for executing the analyzing process, to be described later, is stored in the hard disk 404. The readout device 405 is configured by a CD drive, a DVD drive, or the like, and can read out the computer programs and the data recorded in a recording medium 405a. When the program 404a is recorded in the recording medium 405a, the program 404a read out from the recording medium 405a by the readout device 405 is stored in the hard disk 404.

The image output interface 406 outputs an image signal corresponding to the image data to the display section 41, and the display section 41 displays an image based on the image signal output from the image output interface 406. The user inputs an instruction through the input section 42, and the input/output interface 407 receives the signal input through the input section 42. The communication interface 408 is connected to the measurement unit 2, the transportation unit 3, and the host computer 5, and the CPU 401 transmits and receives the instruction signal and the data with such devices through the communication interface 408.

The optical detector D shown in FIGS. 3A and 3B is also used to acquire the signal for blood cell analysis even when the measurement specimen in which the reagent is not mixed is flowed through the flow cell D1 other than when the measurement specimen in which the reagent is mixed to the blood sample is flowed through the flow cell D1. When the measurement specimen in which the reagent is not mixed is flowed through the flow cell D1, the semiconductor lasers 101 and 103 are driven and the irradiation positions EP1 and EP2 are irradiated with the blue laser light BL and the red laser light RL, respectively. The blue scattered light BS and the red scattered light RS generated from the irradiation positions EP1 and EP2 are respectively received by the light receiving surfaces 205a and 205b of the photodiode 205, and the forward scattered light signals based on the blue scattered light BS and the red scattered light RS are output from the photodiode 205. The bloods cells are classified and counted based on the two types of forward scattered light signals acquired in such manner.

The process of classifying and counting the blood cells based on the two types of forward scattered light signals will be described below. In the following analyzing process, the forward scattered light signals based on the blue scattered light BS and the red scattered light RS are used, but the side scattered light signal based on two types of side scattered lights respectively generated from the blue laser light BL and the red laser light RL may be used for the similar analysis.

First Analyzing Example

The present analyzing example relates to a process of classifying the red blood cells and other blood cells using the red scattered light RS and the blue scattered light BS. In the present analyzing example, only the diluted solution is mixed to the sample aspirated from the sample container T in the preparation of the measurement specimen, and a reagent such as stain, hemolytic agent, and the like is not mixed.

As shown in FIG. 3B, the irradiation position EP1 of the blue laser light BL and the irradiation position EP2 of the red laser light RL are shifted from each other in the Y-axis direction. The measurement specimen flows through the flow path D15 in the positive direction of the Y-axis. Therefore, there is a predetermined time lag from when the blood cells flowing through the flow path D15 is irradiated with the red laser light RL until the blood cells are irradiated with the blue laser light BL. Thus, when using the forward scattered light signals based on the two types of forward scattered lights respectively generated from the blue laser light BL and the red laser light RL for the analysis, the two types of data (hereinafter referred to as "forward scattered light data") acquired from the two types of forward scattered light signals generated from the same blood cell need to be corresponded to each other.

FIGS. 7A and 7B are views describing a method for corresponding the two types of forward scattered light data. FIG. 7A is a timing chart showing the timing at which the red scattered light RS and the blue scattered light BS are detected when the particle concentration is low, and FIG. 7B is a timing chart showing the timing at which the red scattered light RS and the blue scattered light BS are detected when the particle concentration is high (when the blood specimen of normal concentration is used).

With reference to FIG. 7A, when the concentration of the measurement specimen is low, the detection timing of the red scattered light RS and the detection timing of the blue scattered light BS become discrete. In this case, the detection timing of the red scattered light RS with respect to the next blood cell normally does not come in a period between the detection timing of the red scattered light RS and the detection timing of the blue scattered light BS with respect to one blood cell. Therefore, the detection timing of the blue scattered light BS that arrives after the detection timing of the red scattered light RS is corresponded as the detection timing with respect to the same blood cell. In the example of FIG. 7A, the detection timings T21 to T25 are respectively corresponded to the detection timings T11 to T15. The time difference of the detection timing with respect to the same blood cell is substantially the same for any blood cell. Therefore, for example, an average value Δt of the time differences of the two detection timings corresponded to each other can be used as the time difference of the detection timings of the red scattered light RS and the blue scattered light BS with respect to each blood cell.

With reference to FIG. 7B, the detection timing of the red scattered light RS and the detection timing of the blue scattered light BS coexist when the particle concentration is high (when the blood specimen of normal concentration is used). In this case, it is difficult to correspond the detection timing of the red scattered light RS and the detection timing of the blue scattered light BS with respect to the same blood cell. However, the speed of the measurement specimen flowing through the flow cell D1 is nearly unchanged between when the particle concentration is high and when the particle concentration is low. Thus, the time difference Δt acquired when the particle concentration is low can be used as the time difference of the detection timing of the red scattered light RS and the detection timing of the blue scattered light BS with respect to the same blood cell of when the particle concentration is high. In the example of FIG. 7B, the detection timings T2n and T2m are corresponded to the detection timings T1n and T1m, respectively, by using the time difference Δt.

In the present analyzing example, the specimen of low particle concentration is flowed through the flow cell D1 and the time difference Δt is acquired before the blood analysis using the blue scattered light BS and the red scattered light RS is carried out. The time difference Δt acquired in such manner is used when the blood cell analysis using the blue scattered light BS and the red scattered light RS is carried out, and the forward scattered light data acquired based on the blue scattered light BS and the forward scattered light data acquired based on the red scattered light RS are corresponded to each other. This correspondence is carried out in the control section 29 of the measurement unit 2 shown in FIG. 5. The CPU 291 of the control section 29 sequentially corresponds the two types of forward scattered light data based on the red scattered light RS and the blue scattered light BS received from the detecting section 26 (optical detector D) using the time difference Δt, and stores the same in the memory 292.

The method for acquiring the time difference Δt is not limited to the method described above. For example, the speed of the measurement specimen flowing through the flow cell D1 changes depending on the temperature of the measurement specimen. Therefore, a detector for measuring the temperature of the measurement specimen flowing through the flow cell D1 may be arranged in the flow cell D1, and the default value of the time difference Δt may be adjusted based on the detected temperature to acquire the time difference Δt.

The difference between the forward scattered light generated by the red blood cells and the forward scattered light generated by the blood cells other than the red blood cells such as the blood platelets, white blood cells, and the like will now be described.

The scattered light generated from the particle when irradiated with light is defined by the particle diameter and the index of refraction of such particle (Mie scattering theory). The index of refraction can be expressed by a complex number including a real part and an imaginary part. In other words, the complex index of refraction m can be calculated with the following equation where m is the complex index of refraction, $n_r$ is the index of refraction, and $n_i$ is the absorption.

$$m = n_r + in_i$$

According to the above equation, the complex index of refraction m changes according to the absorption so that the index of refraction differs if the degree of absorption of the particle with respect to light differs. Therefore, if different types of particles have different absorption degrees from each other, the scattered light that is generated also differs from each other when such particles are irradiated with light.

Figure 8A:
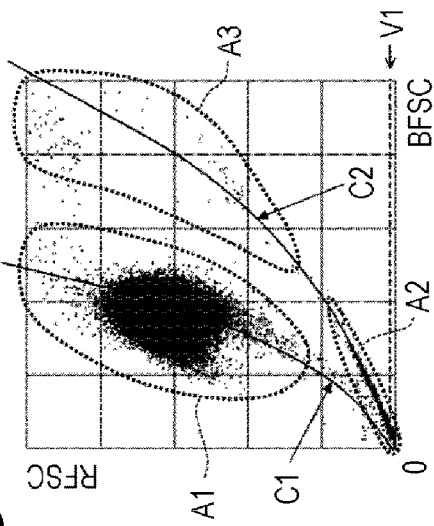
FIG. 8A is a view showing absorption characteristics of hemoglobin contained in the red blood cells according to the first analyzing example.

FIG. 8A is a view showing the absorption characteristics of hemoglobin contained in the red blood cells. The horizontal axis indicates the wavelength of the light irradiated on the hemoglobin, and the vertical axis indicates the absorption coefficient (arbitrary unit).

FIG. 8A shows the absorption coefficients of oxyhemoglobin ($HbO_2$) and deoxyhemoglobin (Hb), respectively. The hemoglobin in the red blood cells are in a state that the oxyhemoglobin and the deoxyhemoglobin coexist, and generally, the hemoglobin oxygen saturation degree of the venous blood is about 75%, that is, the existence ratio of the oxyhemoglobin and the deoxyhemoglobin is 3 to 1. Thus, the property of oxyhemoglobin is dominant in the red blood cells contained in the blood sample.

As shown in FIG. 8A, when the wavelength is within the range of between 400 and 435 nm, the absorption coefficient of the oxyhemoglobin ($HbO_2$) is greater by a few stages compared to the other wavelength bands. When the wavelength is within the range of between 610 and 750 nm, on the other hand, the absorption coefficient of the oxyhemoglobin ($HbO_2$) is smaller by a few stages compared to the other wavelength bands. In other words, the difference between the absorption degree of the red blood cells with respect to the blue laser light BL and the absorption degree of the red blood cells with respect to the red laser light RL becomes large. The difference between the absorption degree of the blood cells other than the red blood cells with respect to the blue laser light BL and the absorption degree of the blood cells other than the red blood cells with respect to the red laser light RL becomes small since the blood cells other than the red blood cells (the blood platelets the white blood cells, and the like) do not contain hemoglobin.

Therefore, the difference between the absorption degree with respect to the blue laser light BL and the absorption degree with respect to the red laser light RL significantly differs between the red blood cells and the blood cells other than the red blood cells (the blood platelets, the white blood cells, and the like), whereby the difference between the intensity of the blue scattered light BS generated when the blue laser light BL is irradiated and the intensity of the red scattered light RS generated when the red laser light RL is irradiated also differs. Specifically, the intensity of the blue scattered light BS tends to be smaller than the intensity of the red scattered light RS in the red blood cells, and the intensity of the blue scattered light BS and the intensity of the red scattered light RS tend to become the same extent in the other blood cells other than the red blood cells.

Figure 8B:
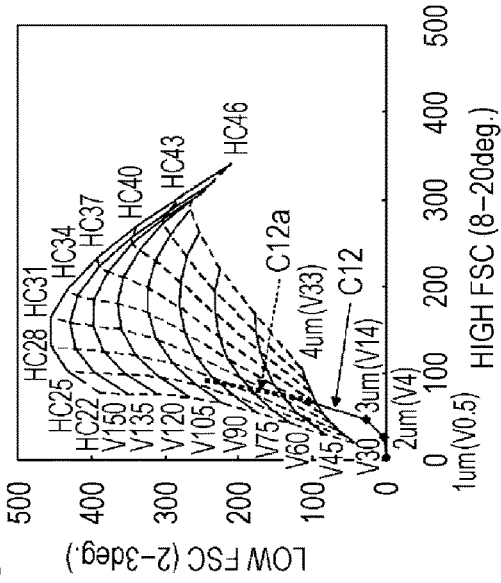
FIGS. 8B and 8C are views showing simulation results of the particle analysis in the first analyzing example and a comparative example, respectively.
Figure 8C:
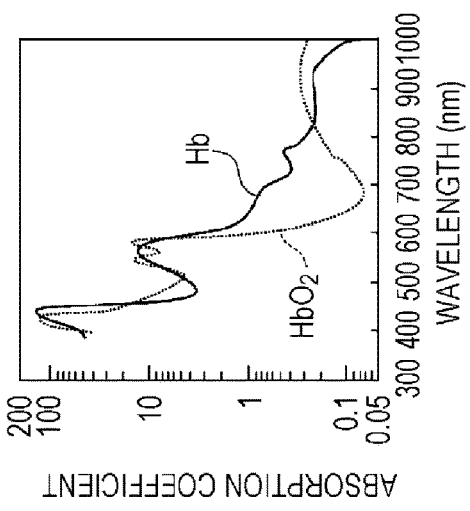

FIGS. 8B and 8C are views respectively showing the simulation result of the particle analysis in the present analyzing example and the comparative example.

The present simulation was conducted with the NA of the forward scattered light receiving optical system D4 as 0.22, the width W1 of the light shielding portion 203c of the beam stopper 203 as 0.3 mm, the space between the flow cell D1 and the beam stopper 203 as 6 mm, and the width in the Y-axis direction of the beam irradiated on the flow cell D1 as 10 µm in the optical detector D. Furthermore, in the present simulation, the particle having properties similar to the red blood cells and the particle having properties similar to the blood platelet were set, and the intensities of the forward scattered light generated when such particles are irradiated with the laser light having a predetermined wavelength were calculated by the simulation.

In the simulation of the present analyzing example, the particles corresponding to the red blood cells and the blood platelets were irradiated with the red laser light RL having the wavelength of 640 nm and the blue laser light BL having the wavelength of 405 nm, and the forward scattered light signals of 640 nm and 405 nm generated by each particle were plotted on the scattergram, as shown in FIG. 8B. In the simulation of the comparative example, the particles corresponding to the red blood cells and the blood platelets were irradiated with the laser light having a wavelength of about 632 nm, and the forward scattered light signals of low angle (2 to 3 degrees) and high angle (8 to 20 degrees) generated by each particle were plotted on the scattergram, as shown in FIG. 8C.

Maps M1 and M2 in which the particles corresponding to the red blood cells are distributed are shown in the scattergrams shown in FIGS. 8B and 8C, respectively. The maps M1 and M2 are created based on 81 particles in which the value of volume is between V30 and V150, and the value of hemoglobin concentration is between HC22 and HC46, where each particle is plotted on the intersection of the lattice of the maps M1 and M2. In the red blood cells of a healthy person, the volume is roughly between V60 and V120, and the hemoglobin concentration is roughly between HC31 and HC37. Distribution lines C11 and C12 in which the particles corresponding to the blood platelets are distributed are shown in the scattergrams shown in FIGS. 8B and 8C, respectively. The distribution lines C11 and C12 are created based on four particles in which the value of the volume is between V0.5 and V33.

As shown in FIGS. 8B and 8C, the red blood cells collected from the subject are also assumed to be distributed in the maps M1 and M2, and the blood platelets collected from the subject are also assumed to be distributed on the distribution lines C11 and C12 from the result of the simulation conducted on the particles corresponding to the red blood cells and the blood platelets.

In the present analyzing example, the map M1 showing the distribution of the red blood cells is positioned on the upper left of the distribution line C11 showing the distribution of the blood platelets, and the map M1 and the distribution line C11 do not overlap. This is assumed to be because the blue laser light BL is absorbed by the hemoglobin contained in the red blood cells and the intensity of the blue scattered light BS is small compared to the red scattered light RS, as described with reference to FIG. 8A. In the comparative example, on the other hand, the map M2 showing the distribution of the red blood cells and the distribution line C12 showing the distribution of the blood platelets are located at similar positions in the left and right direction, and the distribution line C12 is overlapped on the map M2.

In the case of the present analyzing example, the blood platelet is positioned on an extended line C11a of the distribution line C11 if the volume of such blood platelet collected from the subject is large. However, the blood platelet does not overlap the map M1 since the extended line C11a does not intersect with the map M1. Thus, in the present analyzing example, the accuracy in discriminating the red blood cells and the blood platelets is enhanced even if the volume of the blood platelet is large. In the case of the comparative example, for example, the blood platelet is positioned on an extended line C12a of the distribution line C12 if the volume of the blood platelet collected from the subject is large. In this case, the blood platelet may overlap the map M2 since the extended line C12a intersects with the map M2. Thus, in the comparative example, the accuracy in discriminating the red blood cells and the blood platelets may degrade if the volume of the blood platelet is large.

The blood platelets and the white blood cells are assumed to roughly have a similar index of refraction, and also have similar property in that neither the blood platelets nor the white blood cells contain the hemoglobin. Thus, the forward scattered light signal generated from the white blood cell is also assumed to be roughly positioned on the distribution lines C11 and C12. Since the white blood cells are large compared to the blood platelets, the white blood cells are positioned in a region where the values of the red scattered light RS and the blue scattered light BS are large than the blood platelets. In the present analyzing example, the white blood cells are less likely to overlap the map M1, and thus the accuracy in discriminating the red blood cells and the white blood cells is enhanced. In the comparative example, the white blood cells are likely to overlap the map M2, and thus the accuracy in discriminating the red blood cells and the white blood cells may degrade.

Therefore, the red blood cells, and the blood cells other than the red blood cells (the blood platelets and the white blood) cells can be accurately discriminated, as shown in FIG. 8B, by using the blue laser light BL and the red laser light RL as in the present analyzing example.

Figure 8D:
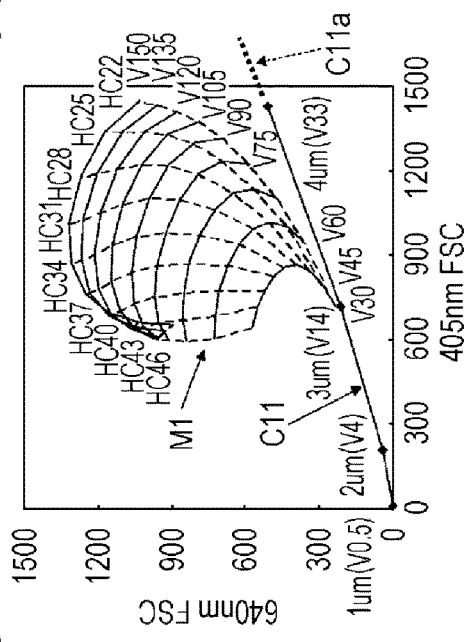
FIG. 8D is a view showing a scattergram based on the forward scattered light according to the first analyzing example.

FIG. 8D is a view showing a scattergram based on the red scattered light RS and the blue scattered light BS obtained from the actual measurement specimen in the present analyzing example. The vertical axis and the horizontal axis indicate the signals of the red scattered light RS and the blue scattered light BS, respectively, output from the photodiode 205, and the blood cells are each plotted on the scattergram with the signals of the red scattered light RS and the blue scattered light BS obtained from each blood cell as parameters.

In this case, the point indicating the red blood cell is distributed in the vicinity of region A1, the point indicating the blood platelet is distributed in the vicinity of region A2, and the point indicating the white blood cell is distributed in the vicinity of region A3. The region A1 in which the red blood cells are distributed is positioned on the distribution curve C1, and the region A2 in which the blood platelets are distributed as well as the region A3 in which the white blood cells are distributed are positioned on the distribution curve C2. The distribution curve C2 corresponds to the distribution line C11 and the extended line C11a shown in FIG. 8B, and the distribution curve C1 and the distribution curve C2 extend at different angles from each other and do not intersect. It is assumed that the distribution curve C1 and the distribution curve C2 are spaced apart from each other as shown in FIG. 8D because the red blood cells contain hemoglobin and the absorption coefficient of hemoglobin greatly changes depending on the wavelength.

Thus, it can be seen that the region A1 in which the red blood cells are distributed positioned on the distribution curve C1, and the regions A2 and A3 in which the blood cells other than the red blood cells are distributed positioned on the distribution curve C2 are less likely to overlap. A threshold value V1 indicating the signal of the red scattered light RS is used to exclude the signal containing noise, as will be described later.

FIG. 9 is a flowchart showing an analyzing process by the blood cell analyzer 1 of the present analyzing example.

When the blood cell analyzer 1 is activated, the time difference Δt is first acquired based on the time difference of the detection timing of the red scattered light RS and the detection timing of the blue scattered light BS (S11), as described with reference to FIGS. 7A and 7B. The acquired time difference Δt is then stored in the memory 292 of the measurement unit 2. The time difference Δt may be, for example, acquired by flowing the accuracy management specimen of low particle concentration through the flow cell D1 or acquired by correcting the default value based on the temperature detected by the detector for measuring the temperature arranged in the flow cell D1.

When the analyzing process is started, the sample container T is taken into the measurement unit 2 and positioned at the position P3, as described above. The CPU 291 of the measurement unit 2 aspirates the sample from the sample container T with the piazza 24a and prepares the measurement specimen from the sample aspirated by the specimen preparing section 25 (S12). The preparation of the measurement specimen in this case is carried out without mixing the reagent for hemolyzing the red blood cells, the reagent for staining the white blood cells, and the like.

The CPU 291 irradiates the flow cell D1 with the red laser light RL and the blue laser light BL, and flows the measurement specimen through the flow cell D1 (S13). The red scattered light RS and the blue scattered light BS, which are two types of forward scattered light, are generated from the same blood cell, and such forward scattered lights are received by the photodiode 205. The CPU 291 acquires the forward scattered light data based on the two types of forward scattered light signal output from the photodiode 205. The CPU 291 then starts to count the elapsed time (S14).

Then, the CPU 291 determines whether the signal of the red scattered light RS is smaller than or equal to the threshold value V1 shown in FIG. 8D (S15). The threshold value V1 is set to a very small value, and is used to exclude the signal containing noise. If the signal of the red scattered light RS is greater than the threshold value V1 (S15: NO), the CPU 291 corresponds the two types of forward scattered light data generated from the same blood cell to each other based on the time difference Δt, and stores the same in the memory 292 (S16). If the signal of the red scattered light RS is smaller than or equal to the threshold value V1 (S15: YES), the CPU 291 proceeds the process to S17 without storing the two types of forward scattered light data for the blood cell in this case.

The processes of S15 and S16 are repeatedly carried out for every blood cell until elapse of a predetermined time (S17). After the measurement has finished with elapse of the predetermined time (S17: YES), the CPU 291 transmits the forward scattered light data stored in the memory 292 to the information processing unit 4 (S18).

When receiving the forward scattered light data from the measurement unit 2 (S21: YES), the CPU 401 of the information processing unit 4 creates a scattergram as shown in FIG. 8D, and displays the same on the display section 41 (S22). Subsequently, the CPU 401 sets the region A1 on the created scattergram (S23). Thus, the CPU 401 sectionalizes the points contained in the region A1 on the scattergram as the red blood cells contained in the measurement specimen, performs the analyzing process of the red blood cells based on the points contained in the region A1 (S24), and displays the analysis result on the display section 41 (S25).

The region A1 set in S23 may be a fixed region defined in advance, or may be a region fine adjusted based on the fixed region. The boundary of the region A1 is defined, for example, by a mathematical equation of line and curve.

For the sake of convenience of explanation, the region A1 is set on the created scattergram, and the points contained in the region A1 on the scattergram are sectionalized as the points corresponding to the red blood cells, but the scattergram does not necessarily need to be created as a figure or a graph, and the setting of the region A1 and the sectionalization of the points contained in the region A1 may be carried out by data processing.

According to the present analyzing example, the blood cells can be satisfactorily classified to the red blood cells and the other blood cells without using reagents such as the stain, the hemolytic agent, and the like. As described above, the red blood cells contain hemoglobin in which the adsorption coefficient greatly changes by wavelength, and thus the intensity of the red scattered light RS and the intensity of the blue scattered light BS greatly differ between the red blood cells and the other blood cells. Thus, the region A1 in which the red blood cells are distributed, and the regions A2 and A3 in which the blood platelets and the white blood cells are distributed are greatly separated, as shown in the scattergram of FIG. 8D. The red blood cells are distributed along the distribution curve C1 schematically shown on the scattergram of FIG. 8D, and the blood platelets and the white blood cells are distributed along the distribution curve C2. As described above, the distribution curve C1 and the distribution curve C2 greatly differ, and the distribution curve C1 and the distribution curve C2 do not intersect. In the scattergram in which the horizontal axis indicates the intensity of the blue scattered light BS and the vertical axis indicates the intensity of the red scattered light RS, the region A1 in which the red blood cells are distributed and the regions A2 and A3 in which the blood platelets and the white blood cells are distributed are greatly separated, as shown in FIG. 8D. Therefore, according to the present analyzing example, the blood cells can be satisfactorily classified to the red blood cells and the other blood cells without using the reagent such as the stain, the hemolytic agent, and the like.

According to the present analyzing example, the red blood cells can be satisfactorily discriminated and counted from the blood cells contained in the measurement specimen with a simple step without using the reagent such as the stain, the hemolytic agent, and the like, by using the blood cell analyzer 1 described in the embodiment. The red blood cells and the blood platelets can be classified from the blood cells contained in the measurement specimen. Furthermore, the blood platelets can be discriminated and counted from the blood cells contained in the measurement specimen.

According to the present analyzing example, the blood platelets and the white blood cells can be discriminated in addition to the red blood cells, as shown in FIG. 8D. However, the number of blood cells of the white blood cells is significantly small compared to the number of blood cells of the red blood cells and the blood platelets, and thus the measurement time needs to be extended and the number of white blood cells contained in the measurement result need to be increased in order to discriminate the white blood cells and obtain highly accurate analysis result according to the present analyzing example. However, if the measurement time is extended, the number of blood cells of the red blood cells and the blood platelets become too large, and the discrimination of the red blood cells and the blood platelets becomes insufficient. The present analyzing example is thus suitably used when efficiently discriminating and classifying the red blood cells and the blood platelets while limiting the measurement time. The white blood cells can be efficiently discriminated and classified by using a second analyzing example described later.

According to the present analyzing example, a step of mixing the reagent to the blood sample can be omitted since the reagent such as the stain, the hemolytic agent, and the like does not need to be used. Thus, the blood cells can be satisfactorily sectionalized with a simple step.

According to the present analyzing example, the cost can be reduced since the reagent such as the stain, the hemolytic agent, and the like does not need to be used. Furthermore, the consumption of reagent can be reduced and the measurement specimen containing the reagent can be suppressed from being discarded, so that an environment friendly analyzing method can be realized.

According to the present analyzing example, the data based on the red scattered light RS and the blue scattered light BS acquired from the same blood cell are corresponded to each other, as described with reference to FIGS. 7A and 7B, and thus the analyzing process can be appropriately carried out even when the concentration of the blood cells is high and the data based on each scattered light coexist.

In the optical detector D according to the present embodiment, the irradiation position EP1 of the blue laser light BL and the irradiation position EP2 of the red laser light RL are shifted in a direction parallel to the flow path D15, as shown in FIG. 3B, whereby the blue scattered light BS and the red scattered light RS can be collected at the light receiving surfaces 205a and 205b, respectively, of the photodiode 205 by adjusting the magnification of the forward scattered light receiving optical system D4 without separately arranging an element for separating the blue scattered light BS and the red scattered light RS. Similarly, the scattered light based on the blue laser light BL and the scattered light based on the red laser light RL can be collected at the light receiving surfaces D54a and D54b, respectively, of the photodiode D54 by adjusting the magnification of the side scattered light receiving optical system D5.

According to the optical detector D of the present embodiment, the light receiving surfaces 205a and 205b are arranged in one photodiode 205, and thus the configuration of the optical detector D can be simplified. Similarly, the configuration of the optical detector D can be simplified since the light receiving surfaces D54a and D54b are arranged in one photodiode D54.

According to the optical detector D of the present embodiment, the configuration of the photodiode 205 can be simplified since the light receiving surfaces 205a and 205b are arranged on the same plane. Similarly, the configuration of the photodiode D54 can be simplified since the light receiving surfaces D54a and D54b are arranged on the same plane.

According to the optical detector D of the present embodiment, the forward light collecting lens 201 has a function of correcting the chromatic aberration with respect to two wavelengths of the red scattered light RS and the blue scattered light BS, and thus the light receiving surfaces 205a and 205b can be appropriately irradiated with the red scattered light RS and the blue scattered light BS. Similarly, the side light collecting lens D53 also has a function of correcting the chromatic aberration with respect to the wavelength of two side scattered lights based on the red laser light RL and the blue laser light BL, and thus the light receiving surfaces D54a and D54b can be appropriately irradiated with the two side scattered lights.

Second Analyzing Example

In the first analyzing example described above, the process of discriminating the red blood cells from the blood cells contained in the measurement specimen using the red scattered light RS and the blue scattered light BS has been described. In the present analyzing example, a process of discriminating the white blood cells from the blood cells contained in the measurement specimen using the red scattered light RS and the blue scattered light BS, and sectionalizing the white blood cells into three classifications will be described. In the present analyzing example as well, only the diluted solution is mixed to the sample aspirated from the sample container T and the reagent such as the stain, the hemolytic agent, and the like is not mixed in the preparation of the measurement specimen, similar to the first analyzing example.

As described above, the white blood cells do not contain hemoglobin, and thus the parameters contributing to the intensity change of the red scattered light RS and the blue scattered light BS with respect to the white blood cells are dominantly the particle diameter. In other words, if the particle diameters are different, the distribution positions of the blood cells on the distribution curve C2 schematically shown in the scattergram of FIG. 8D differ. In the present analyzing example, the white blood cells are sectionalized into lymphocytes, monocytes, and granulocytes (neutrophils, eosinophils, and basophils) based on the difference of such distribution position.

As described in the first analyzing example, the region A1 (distribution curve C1) in which the red blood cells are distributed is greatly separated from the regions A2 and A3 (distribution curve C2) in which other blood cells including the white blood cells are distributed. Thus, when classifying and counting the white blood cells, the data contained in the region A1 in which the red blood cells are distributed can be excluded from the processing target. In the present analyzing example, the acquisition of the forward scattered light data is prohibited for the forward scattered light signal corresponding to the region A1 in which the red blood cells are distributed of the forward scattered light signals output from the photodiode 205, whereby the processing load can be alleviated.

FIGS. 10A to 10C are views showing scattergrams created based on three blood samples collected from different subjects. The vertical axis and the horizontal axis indicate the signals of the red scattered light RS and the blue scattered light BS, respectively, output from the photodiode 205. Dilution is carried out with the diluted solution similar to the analysis of the red blood cells in preparing the measurement specimen of this case, and the measurement is carried out at the measurement time similar to when analyzing the red blood cells in measuring the measurement specimen.

In the present analyzing example, the blood cells in which the signal of the blue scattered light BS is smaller than or equal to a predetermined threshold value V2 are not used for the analyzing process. Specifically, if the signal of the blue scattered light BS output from the photodiode 205 is smaller than or equal to the threshold value V2, the two types of forward scattered light signals acquired from such blood cells are not stored in the memory 292. As shown in FIGS. 10A to 10C, the blood cells are not plotted in the region A10 in which the signal of the blue scattered light BS is smaller than or equal to the threshold value V2 in the scattergram created based on each sample. The threshold value V2 is set to such a value that a majority of red blood cells are contained in the region A10. The region other than the region A10 thus contains a majority of white blood cells. Therefore, as shown in FIGS. 10A to 10C, the blood cells contained in the region A10 are excluded, so that the region A1 in which the red blood cells are distributed is greatly excluded.

FIGS. 10D to 10F are views showing the result of classification of the white blood cells carried out based on the eight blood samples collected from different subjects. The vertical axis and the horizontal axis of FIGS. 10D to 10F respectively indicate the result obtained by the process based on the present analyzing example, and the result obtained by the analyzing method (comparing method) for preparing the measurement specimen using the reagent such as the stain, the hemolytic agent, and the like.

In the present analyzing example, the blood cells smaller than or equal to the threshold value V2 are excluded from the target of analysis, similar to FIGS. 10A to 10C. The number of blood cells in the regions A31 to A33 are each acquired as the number of blood cells of the three classifications (lymphocytes, monocytes, and granulocytes), and the ratio of the number of blood cells of each classification occupied in the total number of blood cells is obtained. The vertical axis of FIGS. 10D to 10F indicates a ratio (%) that the lymphocytes, the monocytes, and the granulocytes occupy in the total number of blood cells in the present analyzing example. In the comparing method as well, the white blood cells are classified into three types according to such method, and the ratio of the number of blood cells of each classification occupied in the total number of blood cells is obtained. The horizontal axis of FIGS. 10D to 10F indicates a ratio (%) that the lymphocytes, the monocytes, and the granulocytes occupy in the total number of blood cells in the present apparatus. Therefore, in FIGS. 10D to 10F, points indicating the ratios corresponding to the eight samples are each plotted with the ratio by the present analyzing example and the ratio by the comparing method as parameters.

In FIGS. 10D to 10F, approximation lines L1 to L3 of the points indicating the ratios of the eight samples, and the equations of the approximation lines L1 to L3 including x (value of horizontal axis) and y (value of vertical axis) are shown. In FIGS. 10D to 10F, the value of correlation coefficient $R^2$ of the result by the present analyzing example and the result by the comparing method is shown. As both of the slope of the approximation line and the value of the correlation coefficient approach one, the correlativity of the result by the present analyzing example and the result by the comparing method becomes high.

As shown in FIGS. 10D to 10F, the slopes of the approximation lines L1 to L3 are 1.1735, 0.9436, and 1.183, respectively, and the value of the correlation coefficient $R^2$ is 0.9397, 0.4948, and 0.9149, respectively, and thus it can be seen that the correlativity of the result of the present analyzing example and the result of the comparing method is relatively high in the lymphocytes and the granulocytes. According to the present analyzing example, it can be seen that the results of the lymphocytes and the granulocytes have an accuracy of the same extent as the comparing method for preparing the measurement specimen using the reagent such as the stain, the hemolytic agent, and the like.

In the monocytes, the convergence degree of each point with respect to the approximation line L2 is slightly low, and thus it can be seen that the correlativity of the result of the present analyzing example and the result of the comparing method is relatively low. However, the analyzing process of the present analyzing example is carried out based on the analyzing method of the red blood cells (dilution and measurement time for the red blood cell), and thus the correlativity of the present analyzing example and the comparing method may be enhanced by carrying out the analyzing process of the present analyzing example based on the analyzing method of the white blood cells (dilution and measurement time for the white blood cell).

Figure 11:
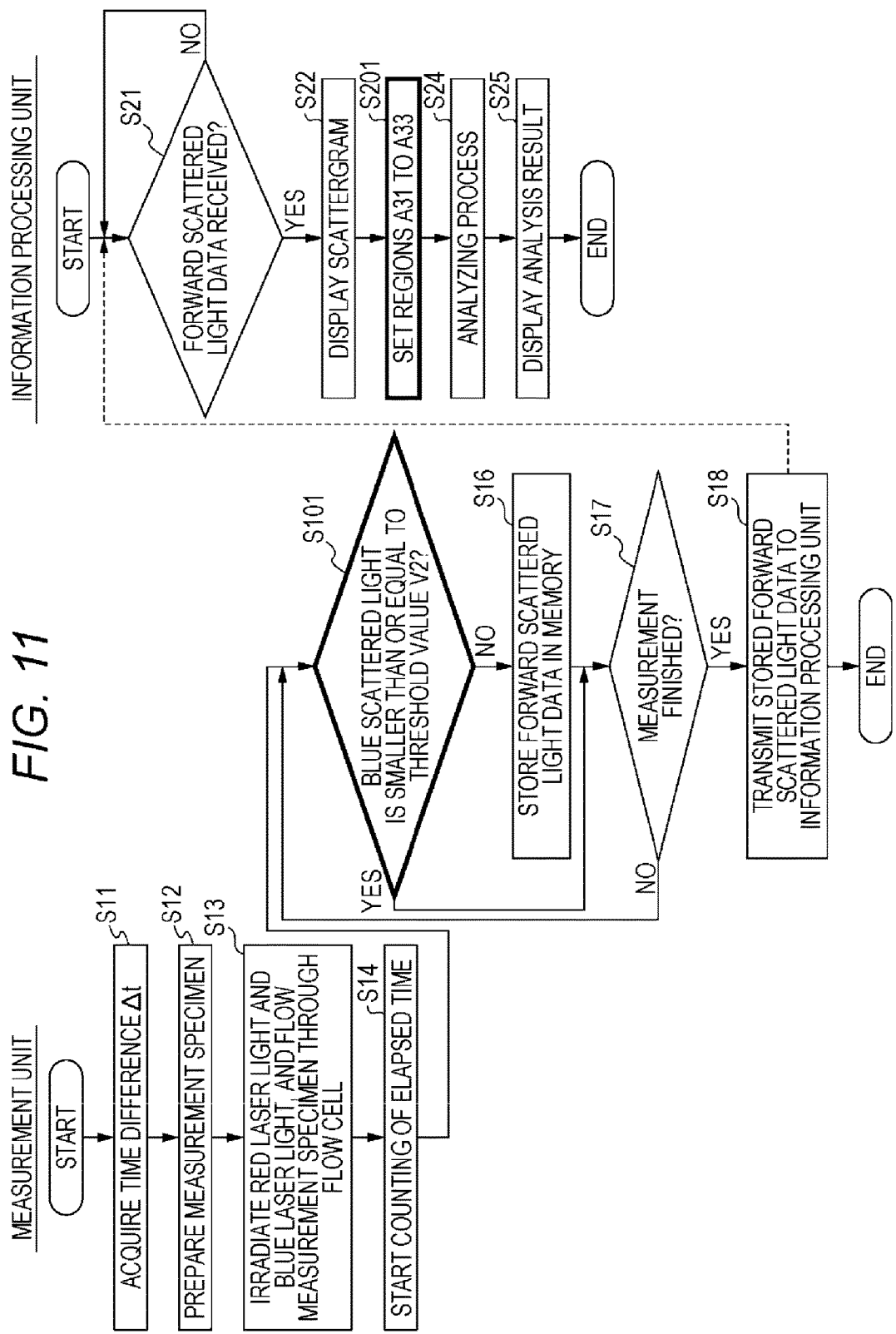
FIG. 11 is a flowchart showing an analyzing process by the blood cell analyzer according to the second analyzing example.

FIG. 11 is a flowchart showing the analyzing process by the blood cell analyzer 1 of the present analyzing example. In the flowchart shown in FIG. 11, S101 is added in place of S15, and S201 is added in place of S23 with respect to the flowchart of the first analyzing example shown in FIG. 9.

The CPU 291 of the measurement unit 2 carries out the processes of S11 to S14, similar to the first analyzing example. Thereafter, the CPU 291 determines whether or not the signal of the blue scattered light BS is smaller than or equal to the threshold value V2 shown in FIGS. 10A to 10C (S101). If the signal of the blue scattered light BS is greater than the threshold value V2 (S101: NO), the CPU 291 corresponds the two types of forward scattered light data generated from the same blood cell with respect to each other based on the time difference Δt, and stores the same in the memory 292 (S16). If the signal of the blue scattered light BS is smaller than or equal to the threshold value V2 (S101: YES), the CPU 291 proceeds the process to S102 without storing the two types of forward scattered light data for the relevant blood cell.

The processes of S201 and S16 are repeatedly carried out for every blood cell until elapse of a predetermined time (S17). The predetermined time in this case is set to be longer than the predetermined time set in S17 (see FIG. 9) of the first analyzing example, in order to detect greater number of white blood cells, which number is by a few stages less than the red blood cells. After the measurement has finished with elapse of the predetermined time (S17: YES), the CPU 291 transmits the forward scattered light data stored in the memory 292 to the information processing unit 4 (S18).

When receiving the forward scattered light data from the measurement unit 2 (S21: YES), the CPU 401 of the information processing unit 4 creates the scattergrams as shown in FIGS. 10A to 10C, and displays the same on the display section 41 (S22). The CPU 401 then sets the regions A31 to A33 (region A3) on the created scattergrams (S201). Thus, the CPU 401 sectionalizes the points included in the regions A31 to A33 to the lymphocytes, the monocytes, and the granulocytes (neutrophils, eosinophils, and basophils) contained in the measurement specimen, carries out the analyzing process of the white blood cells based on the points included in the regions A31 to A33 (S24), and displays the analysis result on the display section 41 (S25).

The regions A31 to A33 set in S201 may be fixed regions defined in advance, or may be regions fine adjusted based on the fixed regions. The boundary of the regions A31 to A33 is defined, for example, by the mathematical equation of line and curve.

For the sake of convenience of explanation, the regions A31 to A33 are set on the created scattergrams, and the points included in the regions A31 to A33 on the scattergram are sectionalized as points corresponding to the lymphocytes, the monocytes, and the granulocytes, respectively, but the scattergram does not necessarily need to be created as a figure or a graph, and the setting of the regions A31 to A33 and the sectionalization of the points included in the regions A31 to A33 may be carried out by data processing.

According to the present analyzing example, the white blood cells can be sectionalized to the lymphocytes, the monocytes, and the granulocytes (neutrophils, eosinophils, and basophils) without using the reagent such as the stain, the hemolytic agent, and the like, and then counted. Furthermore, the white blood cells can be satisfactorily discriminated from the blood cells contained in the measurement specimen, and the white blood cells can be sectionalized into three classifications and counted with a simple step, without using the reagent such as the stain, the hemolytic agent, and the like, by using the optical detector D having the configuration shown in FIGS. 3A and 3B.

Furthermore, according to the present analyzing example, the forward scattered light data of the blood cell are not stored in the memory 292 if the signal of the blue scattered light BS is smaller than or equal to the threshold value V2. The forward scattered light data that is not necessary in the analyzing process of the white blood cells are thus not stored, whereby the white blood cells can be efficiently discriminated from the blood cells contained in the measurement specimen and counted while reducing the load of the analyzing process.

Third Analyzing Example

In the second analyzing example, the process of discriminating the white blood cells from the blood cells contained in the measurement specimen using the red scattered light RS and the blue scattered light BS, and sectionalizing the white blood cells into three classifications has been described. In the present analyzing example, a process of simultaneously performing the process of discriminating the red blood cells from the blood cells contained in the measurement specimen using the red scattered light RS and the blue scattered light BS and the process of discriminating the white blood cells and sectionalizing the white blood cells into three classifications using one measurement specimen will be described. In the present analyzing example as well, only the diluted solution is mixed to the sample aspirated from the sample container T and the reagent such as the stain, the hemolytic agent, and the like is not mixed in the preparation of the measurement specimen, similar to the first and second analyzing examples.

Figure 12:
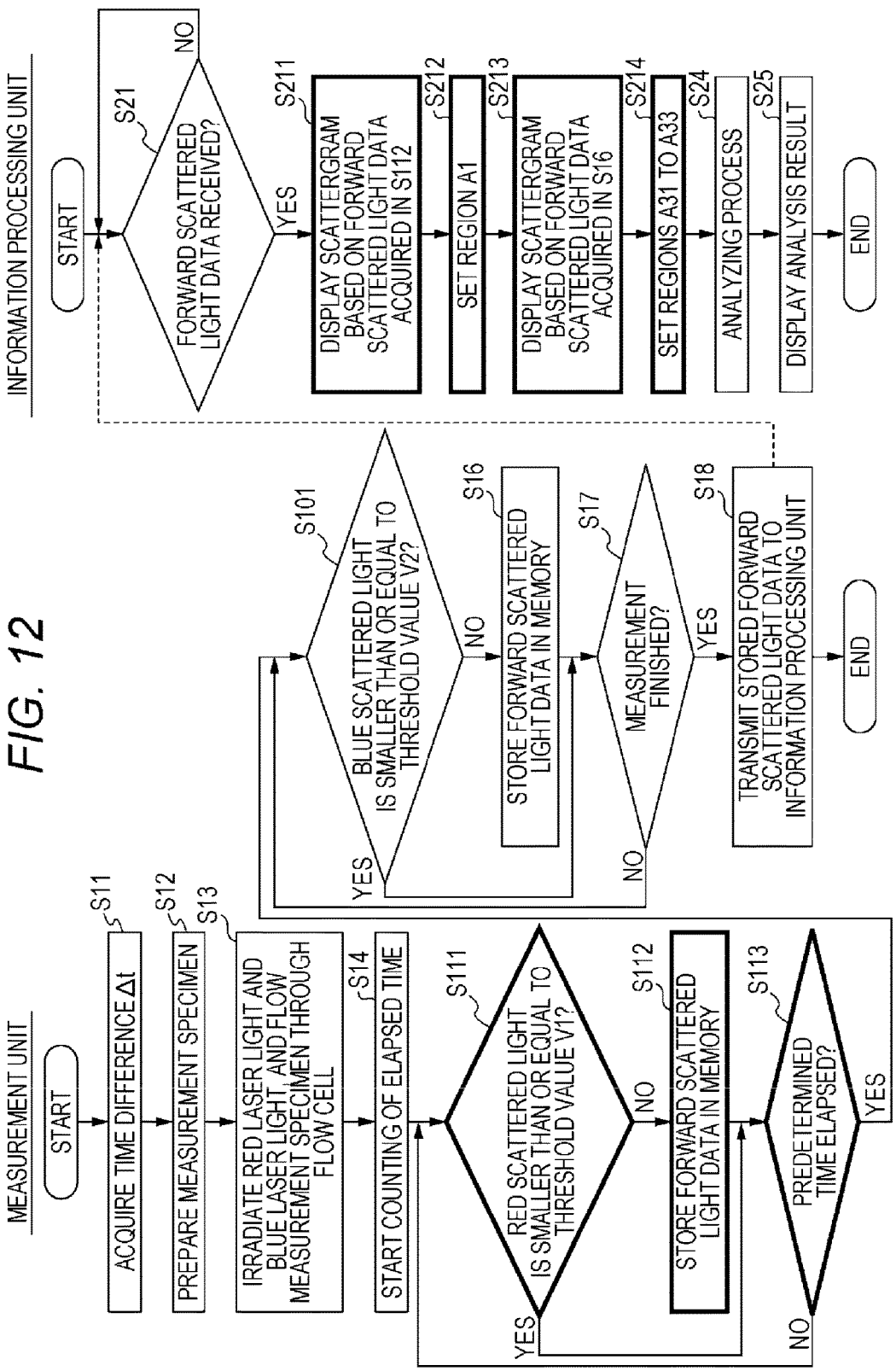
FIG. 12 is a flowchart showing an analyzing process by a blood cell analyzer according to a third analyzing example.

FIG. 12 is a flowchart showing the analyzing process by the blood cell analyzer 1 of the present analyzing example. In the flowchart shown in FIG. 12, S111 to S113 are added between S14 and S101, and S211 to S214 are added in place of S22 and S201 with respect to the flowchart of the second analyzing example shown in FIG. 11.

The CPU 291 of the measurement unit 2 performs the processes of S11 to S14, similar to the first and second analyzing examples. The CPU 291 then determines whether or not the signal of the red scattered light RS is smaller than or equal to the threshold value V1 shown in FIG. 8D (S111), similar to S15 of FIG. 9. If the signal of the red scattered light RS is greater than the threshold value V1 (S111: NO), the CPU 291 corresponds two types of forward scattered light data generated from the same blood cell to each other based on the time difference Δt, and stores the same in the memory 292 (S112), similar to S16 of FIG. 9. If the signal of the red scattered light RS is smaller than or equal to the threshold value V1 (S111: YES), the CPU 291 proceeds the process to S104 without storing the two types of forward scattered light data for the blood cell in this case.

Thus, the processes of S111 and S112 are repeatedly carried out for every blood cell until elapse of a predetermined time (S113). After the measurement has finished with elapse of the predetermined time (S113: YES), the process proceeds to S101. The supply of the measurement specimen to the flow cell D1 is continued.

The CPU 291 then determines whether or not the signal of the blue scattered light BS is smaller than or equal to the threshold value V2 (S101), similar to the second analyzing example. The forward scattered light data is stored in the memory 292 (S16) if the signal of the blue scattered light BS is greater than the threshold value V2 (S101: NO), and the two types of forward scattered light data for the blood cell are not stored if the signal of the blue scattered light BS is smaller than or equal to the threshold value V2 (S101: YES). After the measurement has finished with elapse of the predetermined time (S17: YES), the CPU 291 transmits the forward scattered light data stored in the memory 292 in S112 and the forward scattered light data stored in the memory 292 in S16 to the information processing unit 4 (S18).

When receiving the forward scattered light data from the measurement unit 2 (S21: YES), the CPU 401 of the information processing unit 4 creates the scattergram as shown in FIG. 8D based on the forward scattered light data acquired in S112, and displays the same on the display section 41 (S211). The CPU 401 then sets the region A1 on the scattergram created in S211 (S212). The CPU 401 then creates the scattergram as shown in FIGS. 10A to 10C based on the forward scattered light data acquired in S16, and displays the same on the display section 41 (S213). The CPU 401 then sets the regions A31 to A33 (region A3) on the scattergram created in S213 (S214).

The CPU 401 then performs the analyzing process of the red blood cells, similar to the first analyzing example, based on the scattergram created in S211 and the region A1 set in S212, and performs the analyzing process of the white blood cells, similar to the second analyzing example, based on the scattergram created in S213 and the regions A31 to A33 set in S214 (S24). The CPU 401 then displays the analysis result on the display section 41 (S25).

According to the present analyzing example, the red blood cells can be discriminated and the white blood cells can be discriminated from the blood cells contained in the measurement specimen, and the white blood cells can be sectionalized into the lymphocytes, the monocytes, and the granulocytes (neutrophils, eosinophils, and basophils) and counted without using the reagent such as the stain, the hemolytic agent, and the like.

Furthermore, according to the present analyzing example, both the forward scattered light data necessary for the discrimination of the white blood cells and the forward scattered light data necessary for the discrimination of the red blood cells can be acquired in one measurement step. Thus, the discrimination of the white blood cells and the discrimination of other blood cells (red blood cells) other than the white blood cells can be carried out using the same measurement specimen, whereby the measurement specimen does not need to be individually prepared in order to perform the discrimination of the white blood cells and the discrimination of the other blood cells other than the white blood cells.

Light Irradiation Unit

In the embodiment described above, the flow cell D1 is irradiated with the red laser light RL and the blue laser light BL such that the irradiation positions in the flow path D15 are shifted in the Y-axis direction, as shown in FIG. 4A. In this case, the irradiation position of the blue laser light BL is adjusted with the optical axis of the red laser light RL as a reference. In other words, after the intensity peak position of the red laser light RL is positioned at the middle of the flow path D15, the irradiation position of the blue laser light BL is adjusted so that the intensity peak position of the blue laser light BL is at the middle of the flow path D15. Therefore, the irradiation position of the blue laser light needs to be adjusted not only in the Y-axis direction but also in the X-axis direction.

The configuration of the light irradiation unit UD capable of adjusting the irradiation position of the blue laser light in the X-axis direction and in the Y-axis direction will be described below.

Figure 13:
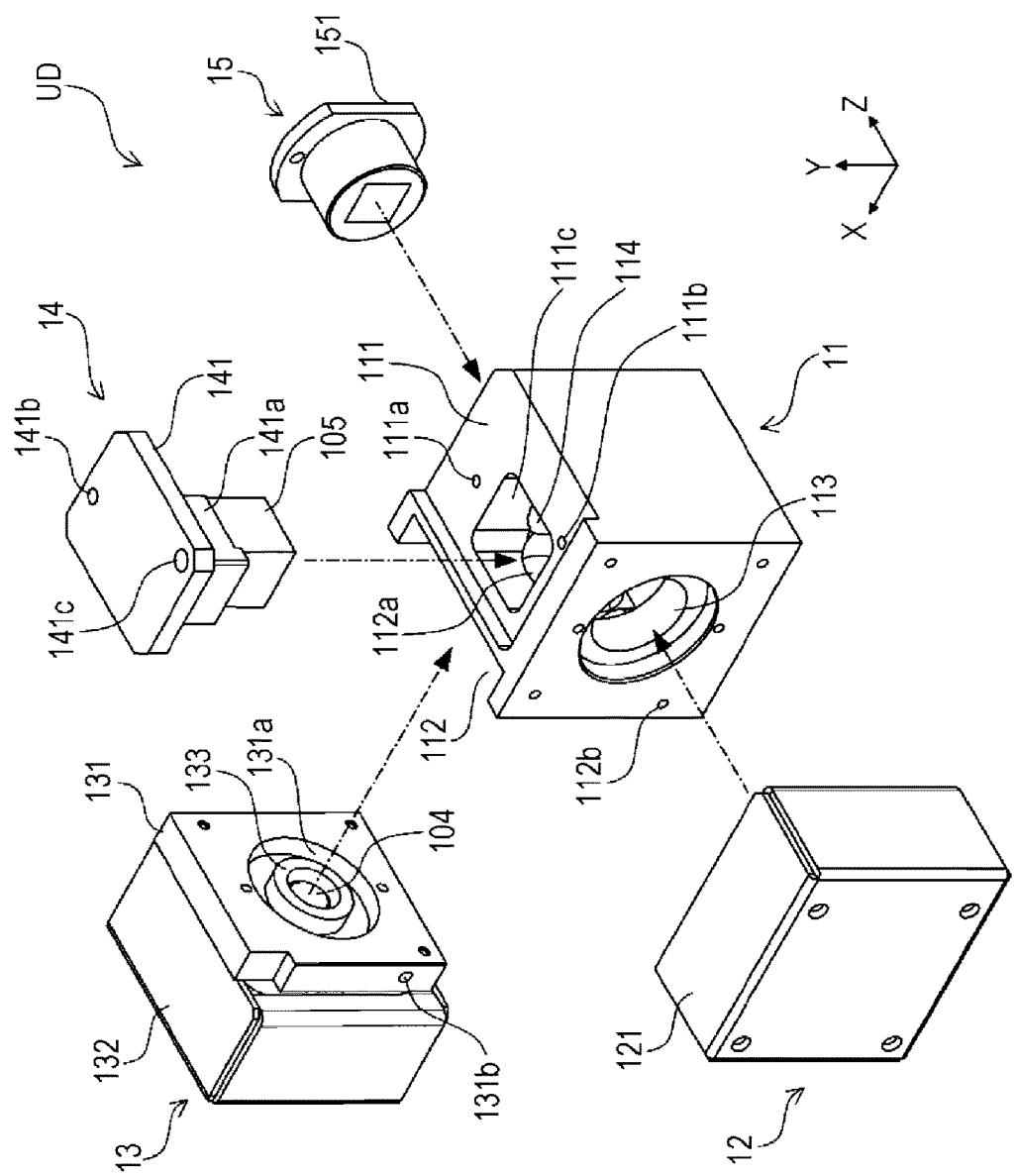
FIG. 13 is an exploded perspective view showing a configuration example of a light irradiation unit according to the present embodiment.

FIG. 13 is an exploded perspective view showing a configuration example of the light irradiation unit UD. The light irradiation unit UD is obtained by unitizing the light irradiation optical system D3 shown in FIG. 3A.

As shown in FIG. 13, the light irradiation unit UD includes a base 11, a red light source unit 12, a blue light source unit 13, a dichroic mirror unit 14, and a light collecting lens unit 15.

The base 11 includes a hollow member having a substantially cube shape, where a step portion 111, which is one stage lower, is formed on the upper surface of the base 11, and two screw holes 111a, 111b and an opening 111c communicating to the interior are formed in the step portion 111. The bottom surface of the step portion 111 is parallel to the X-Z plane. A recess 112 recessed in the negative direction of the X-axis is formed in the side surface on the positive side of the X-axis of the base 11. A surface (bottom surface) on the negative side of the X-axis of the recess 112 is parallel to the Y-Z plane, and each surface (wall surface) on the positive and negative side of the X-axis of the recess 112 is parallel to the X-Y plane. A circular opening 112a is formed in the bottom surface of the recess 112. A screw hole 112b that passes through to the side surface on the negative side of the Z-axis of the base 11 is provided on the wall surface on the negative side of the Z-axis of the recess 112. Furthermore, circular holes 112c, 112d (not shown in FIG. 13, see FIG. 16C) that pass through to the side surface on the positive side of the Z-axis of the base 11 are provided on the wall surface on the positive side of the Z-axis of the recess 112. Furthermore, a circular opening 113 communicating to the interior is formed in the side surface on the negative side of the Z-axis of the base 11. A circular opening 114 (not shown in FIG. 13, see FIG. 14B) communicating to the interior is also formed in the side surface on the positive side of the Z-axis of the base 11.

The red light source unit 12 includes a semiconductor laser 101 and a collimator lens 102 shown in FIG. 3, and a cover 121 for accommodating the same.

The blue light source unit 13 includes a semiconductor laser 103 and a collimator lens 104 shown in FIG. 3, a plate-shaped supporting body 131 for supporting the same, and a cover 132 for accommodating the semiconductor laser 103 and the collimator lens 104. The semiconductor laser 103 and the collimator lens 104 are held by the holder 133, and the holder 133 is attached to the supporting body 131. An opening 131a is provided at a substantially central position in the supporting body 131, and a circular hole 131b is formed in the side surface on the negative side of the Z-axis. Two screw holes 131c, 131d (not shown in FIG. 13, see FIG. 16B) are formed in the side surface on the positive side of the Z-axis of the supporting body 131.

The dichroic mirror unit 14 includes a dichroic mirror 105, and a supporting body 141 for supporting the dichroic mirror 105. The dichroic mirror 105 has a cubic shape, and interiorly includes a mirror surface that transmits the red laser light RL and reflects the blue laser light BL. The supporting body 141 has a configuration in which a cuboid shaped seat 141a is integrally formed on the lower surface of the plate-shaped member. The cubic shaped dichroic mirror 105 is attached to the seat 141a. Furthermore, holes 141b, 141c are formed in the supporting body 141 at positions corresponding to the two screw holes 111a, 111b formed in the upper surface of the base 11.

The light collecting unit 15 includes a cylindrical lens 106 and a condenser lens 107 shown in FIG. 3, and a holder 151 for holding the same.

The light irradiation unit UD is assembled by attaching each of the red light source unit 12, the blue light source unit 13, the dichroic mirror unit 14, and the light collecting lens unit 15 to the corresponding side surfaces of the base 11.

FIG. 14A is a perspective view showing the light irradiation unit UD after the assembly, and FIG. 14B is a cross-sectional view schematically showing the main configuration of the light irradiation unit UD after the assembly. FIG. 14B schematically shows the cross-section of when the vicinity of the middle of the light irradiation unit UD is cut by a plane parallel to the X-Z plane, where the supporting body 141 of the dichroic mirror unit 14 and the dichroic mirror 105 are simultaneously shown for the sake of convenience.

With reference to FIG. 14B, the semiconductor laser 101 and the collimator lens 102 are held by the holder 122, and supported by the base 11 by attaching the holder 122 to the base 11. The holder 122 includes a cylindrical portion, and a collar portion in which the diameter is greater than the cylindrical portion, where the collar portion is screw-fitted to the base 11 with the cylindrical portion fitted into the opening 113 of the base 11. The holder 122 is thereby attached to the base 11. After the holder 122 is attached to the base 11, the cover 121 (see FIG. 14A) is attached to the holder 122.

The cylindrical lens 106 and the condenser lens 107 are held by the holder 151, and supported by the base 11 by attaching the holder 151 to the base 11. The holder 151 includes a cylindrical portion, and a collar portion in which the width is wider than the cylindrical portion, where the collar portion is screw-fitted to the base 11 with the cylindrical portion fitted into the opening 114 of the base 11. The holder 151 is thereby attached to the base 11.

The semiconductor laser 103 and the collimator lens 104 are supported by the holder 133, and the holder 133 is attached to the supporting body 131. Furthermore, the cover 132 (see FIG. 14A) is attached to the supporting body 131. The supporting body 131 is inserted into the recess 112 of the base 11 and assembled to the base 11. The supporting body 131 is assembled to the base 11 so as to be turnable about a rotation axis RA1. The method for assembling the supporting body 131 will be described later with reference to FIGS. 16A to 16C.

With reference to FIG. 14A, the dichroic mirror unit 14 is attached to the step portion 111 of the upper surface of the base 11 by a spring washer 142 and a nut 143. More specifically, the seat 141a and the dichroic mirror 105 shown in FIG. 13 are inserted into the opening 111c at the upper surface of the base 11, and the supporting body 141 is mounted on the upper surface of the step portion 111. The holes 141b and 141c of the supporting body 141 are each aligned with the screw holes 111a, 111b on the base 11 side. The nut 143 is screw-fastened to one screw hole 111a through the spring washer 142, and the nut 143 is also screw-fastened to the other screw hole 111a through the spring washer 142, in such state. The dichroic mirror unit 14 is assembled to the base 11 in such manner. Further, a washer (not shown) is inserted between the two spring washers 142 and the upper surface of the supporting body 141.

When assembling the dichroic mirror unit 14 to the base 11, the two nuts 143 are loosely screw-fastened. As shown in FIG. 13, the hole 141c of the two holes 141b and 141c formed in the supporting body 141 has a greater diameter compared to the hole 141b. The diameter of the screw portion of the two nuts 143 shown in FIG. 14A is substantially the same as the diameter of the hole 141b shown in FIG. 13. Thus, when the two nuts 143 are loosely screw-fastened, the supporting body 141 can turn by a predetermined angle range about the rotation axis RA1 passing through the center of the hole 141b.

FIG. 15A is a perspective view showing a state before the light irradiation unit UD is installed in a position adjustment mechanism PA, and FIG. 15B is a perspective view showing a state in which the light irradiation unit UD is installed in the position adjustment mechanism PA.

With reference to FIG. 15A, the position adjustment mechanism PA includes a first adjustment plate 161, two plate springs 162, a second adjustment plate 171, and two plate springs 172.

The first adjustment plate 161 includes a thin plate-shaped member, and has a contour in which a part of a square is cutout in plane view. The first adjustment plate 161 is formed with a long hole 161a, which extends in the X-axis direction, and a cutout 161b, which also extends in the X-axis direction, and is also formed with two wall portions 161c and 161d that project out in the positive direction of the Y-axis and extend in the Z-axis direction at the end on the negative side of the X-axis. Furthermore, the first adjustment plate 161 is formed with two screw holes 161e, 161f. The second adjustment plate 171 includes a thin plate-shaped member, and has a contour in which a part of a rectangle is cutout in plane view. The second adjustment plate 171 is formed with an opening 171a at a position corresponding to the long hole 161a, and is also formed with a long hole 171b, which extends in the Z-axis direction, and a cutout 171c, which also extends in the Z-axis direction, at positions corresponding to the screw holes 161e, 161f.

The first adjustment plate 161 is attached to a supporting substrate (not shown) arranged in the blood cell analyzer 1. More specifically, the end on the positive side of the Z-axis of the first adjustment plate 161 is pushed against the wall surface (not shown) arranged in the supporting substrate and extended in the X-axis direction. In this state, the nut 164 is inserted into the long hole 161a through the spring washer 163, and the nut 164 is also inserted into the cutout 161b through the spring washer 163, as shown in FIG. 15B. In this case, the washer (not shown) is inserted between the spring washer 163 and the upper surface of the first adjustment plate 161. The two nuts 164 are fitted into the screw holes (not shown) formed in the supporting substrate, and the nut 164 is fastened to the screw hole to assemble the first adjustment plate 161 to the supporting substrate. Furthermore, the two plate springs 162 are attached to the supporting substrate to hold down the end on the negative side of the Z-axis of the first adjustment plate 161. The first adjustment plate 161 is held down in the negative direction of the Y-axis, and also held down in the positive direction of the Z-axis by the plate springs 162.

After the first adjustment plate 161 is attached to the supporting substrate, the second adjustment plate 171 is attached to the upper surface of the first adjustment plate 161. In other words, the end on the negative side of the X-axis of the second adjustment plate 171 is pushed against the inner wall surface of the wall portions 161c and 161d of the first adjustment plate 161. In this state, the nut 174 is inserted into the long hole 171c through the spring washer 173, and the nut 174 is also inserted into the cutout 171b through the spring washer 173, as shown in FIG. 15B. In this case, the washer (not shown) is inserted between the spring washer 173 and the upper surface of the second adjustment plate 171. The two nuts 174 are fitted into the screw holes 161e and 161f formed in the first adjustment plate 161, and the nut 174 is fastened to the screw holes 161e and 161f to assemble the second adjustment plate 171 to the first adjustment plate 161. Furthermore, the two plate springs 172 are attached to the first adjustment plate 161 to hold down the end on the positive side of the X-axis of the second adjustment plate 171. The second adjustment plate 171 is held down in the negative direction of the Y-axis, and also held down in the negative direction of the X-axis by the plate springs 172.

After the second adjustment plate 171 is attached to the upper surface of the first adjustment plate 161, the light irradiation unit UD is attached to the upper surface of the second adjustment plate 171. A state shown in FIG. 15B is thereby obtained.

In the state of FIG. 15B, the nut 164 is loosely screw-fastened. Thus, the first adjustment plate 161 can move in the X-axis direction while the end on the positive side of the Z-axis slidably contacts the wall surface (not shown) of the supporting substrate. Similarly, the nut 174 is loosely screw-fastened, so that the second adjustment plate 171 can move in the Z-axis direction while the end on the negative side of the X-axis slidably contacts the inner wall surface of the wall portions 161c and 161d of the first adjustment plate 161.

After the light irradiation unit UD is attached to the second adjustment plate 171, the position adjustment of the red laser light RL and the blue laser light BL with respect to the flow path D15 of the flow cell D1 is carried out. First, the semiconductor laser 101 is lighted and the position adjustment of the red laser light RL is carried out. Specifically, the position in the Z-axis direction of the first adjustment plate 161 is adjusted such that the red laser light RL is focused on the flow path D15 of the flow cell D1. The position in the X-axis direction of the second adjustment plate 171 is adjusted such that the intensity peak position of the red laser light RL is positioned at the middle of the flow path D15. After the position adjustment of the first adjustment plate 161 and the second adjustment plate 171 is completed, the nut 164 is tightened to fix the first adjustment plate 161 to the supporting substrate, and furthermore, the nut 174 is tightened to fix the second adjustment plate 171 to the first adjustment plate 161. The position adjustment of the red laser light RL is thereby completed. Thereafter, the semiconductor laser 103 is lighted and the position adjustment of the blue laser light BL is carried out.

Figure 16A:
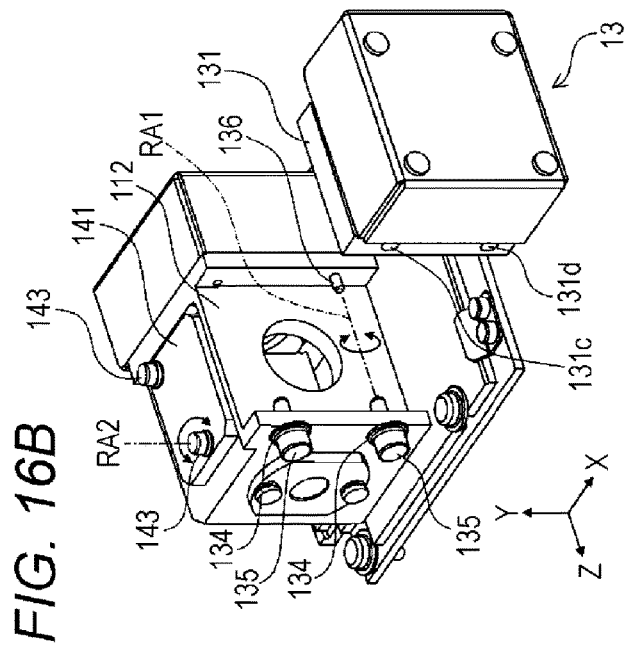
FIG. 16A is a perspective view showing a state in which the light irradiation unit according to the present embodiment is installed in the position adjustment mechanism.
Figure 16B:
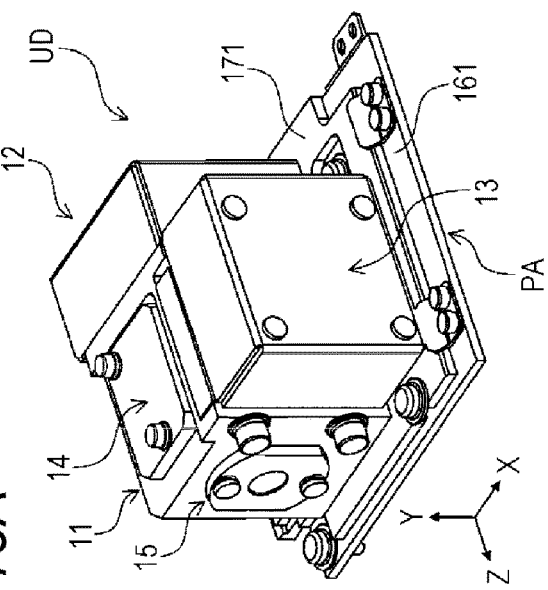
FIG. 16B is a perspective view showing a state in which a blue light source unit is detached from the state of FIG. 16A.
Figure 16C:
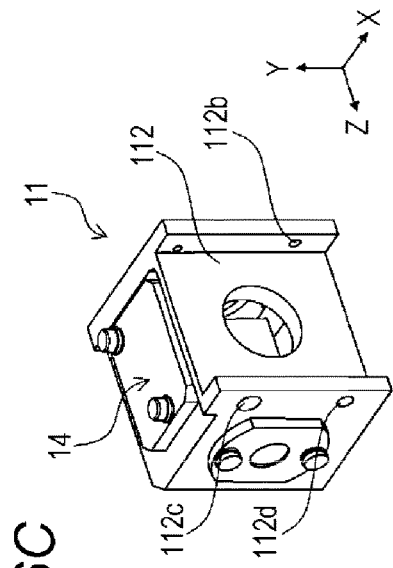
FIG. 16C is a perspective view showing the vicinity of a recess of the base.

FIG. 16A is a perspective view of a state in which the light irradiation unit UD is installed in the position adjustment mechanism PA seen from the blue light source unit 13 side, FIG. 16B is a perspective view showing a state in which the blue light source unit 13 is removed from the state of FIG. 16A, and FIG. 16C is a perspective view showing the vicinity of the recess 112 of the base 11.

With reference to FIG. 16B, after the supporting body 131 is inserted into the recess 112, the blue light source unit 13 is attached to the base 11 by the nuts 135 and 136. In this case, the two screw holes 131c, 131d arranged on the surface on the positive side of the Z-axis of the supporting body 131 are respectively aligned with the holes 112c, 112d (see FIG. 16C) on the base 11 side, and the hole 131b (see FIG. 13) arranged on the surface on the negative side of the Z-axis of the supporting body 131 is aligned with the screw hole 112b (see FIG. 16C) on the base 11 side. The two nuts 135 are respectively passed through the holes 112c, 112d, and fastened to the screw holes 131c, 131d on the supporting body 131 side, and furthermore, the nut 136 is passed through the screw hole 112b and inserted into the hole 131b on the supporting body 131 side.

A spring washer 134, and a washer (not shown) are interposed in order from the negative side of the Z-axis between the nut 135 and the side surface on the positive side of the Z-axis of the base 11. The nut 135 and the nut 136 on the negative side of the Y-axis are arranged to linearly line in the Z-axis direction. The diameter of the hole 131b on the supporting body 131 side is substantially the same as the diameter of the screw portion of the nut 136. Furthermore, as shown in FIG. 16C, the diameter of the hole 112c on the upper side of the base 11 is greater than the diameter of the hole 112d on the lower side. The diameter of the hole 112d on the lower side is substantially the same as the diameter of the screw portion of the nut 135. Therefore, when the two nuts 135 are loosely fastened, the blue light source unit 13 can turn by a predetermined angle range about the rotation axis RA1 of FIG. 16C.

The position adjustment of the blue laser light BL with respect to the flow path D15 of the flow cell D1 is carried out with the two nuts 135 loosely fastened. In this case, the nut 143 of the dichroic mirror unit 14 is also loosely fastened, as described above, and the supporting body 141 and the dichroic mirror 105 (see FIG. 13) can turn about a rotation axis RA2.

Figure 17A:
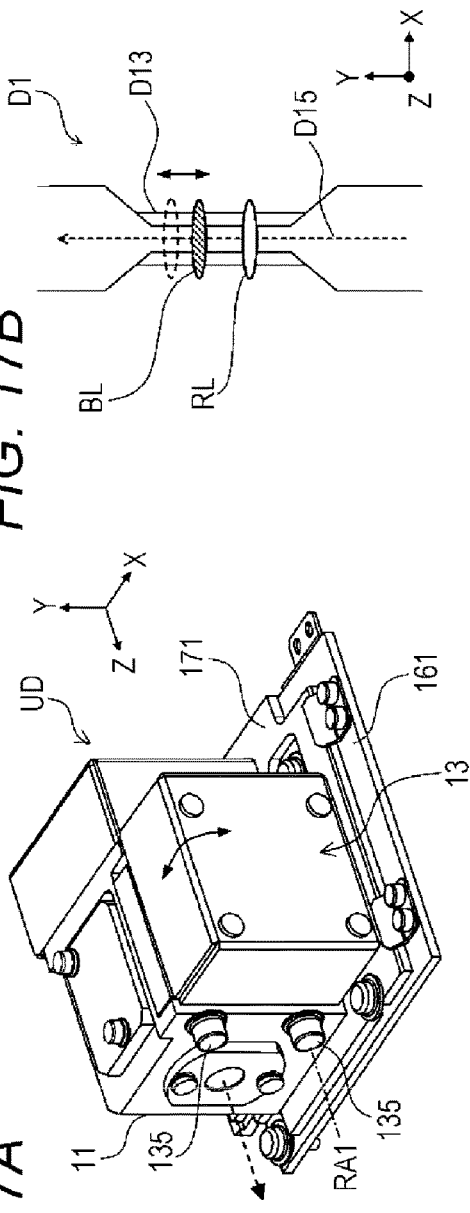
FIGS. 17A and 17B are views showing a position adjustment method in the Y-axis direction of the blue laser light in the irradiation unit according to the present embodiment.
Figure 17B:
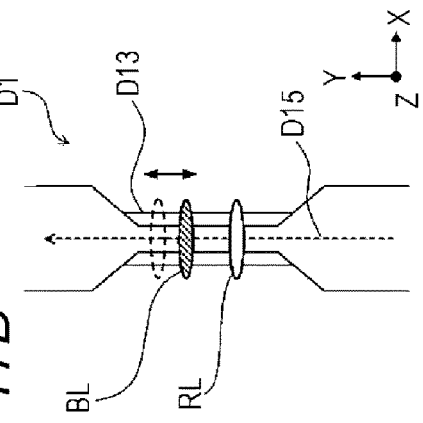
Figure 17C:
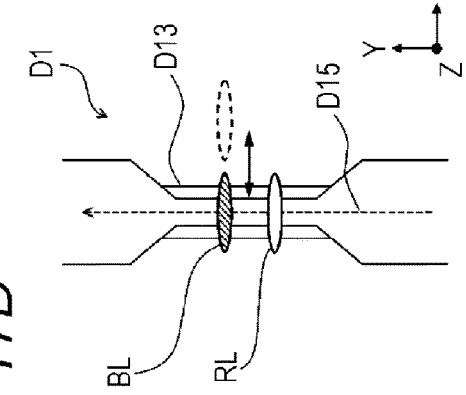
FIGS. 17C and 17D are views showing the position adjustment method in the X-axis direction of the blue laser light in the light irradiation unit according to the present embodiment.
Figure 17D:
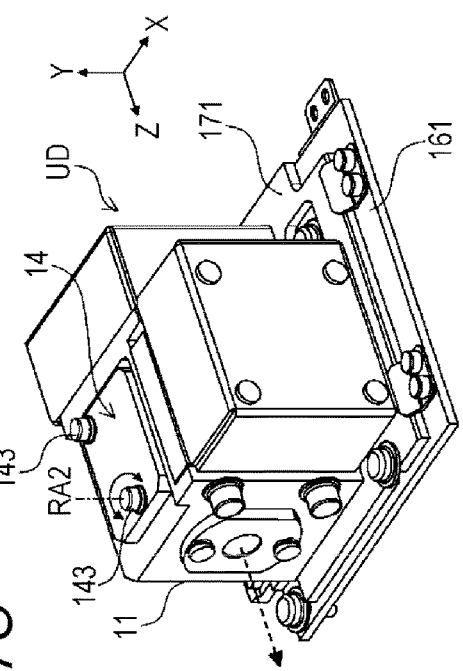

FIGS. 17A and 17B are views showing a position adjustment method in the Y-axis direction of the blue laser light BL in the light irradiation unit UD, and FIGS. 17C and 17D are views showing a position adjustment method in the X-axis direction of the blue laser light BL in the light irradiation unit UD.

With reference to FIG. 17A, when the blue light source unit 13 is rotated about the rotation axis RA1, the optical axis of the blue laser light BL entering the dichroic mirror 105 of the dichroic mirror unit 14 turns in a direction parallel to the X-Y plane. Thus, the optical axis of the blue laser light BL entering the condenser lens 107 of the light collecting lens unit 15 turns in a direction parallel to the Y-Z plane, and the irradiation position of the blue laser light BL with respect to the flow cell D1 displaces in a direction (Y-axis direction) parallel to the flow path D15, as shown in FIG. 17B.

With reference to FIG. 17C, when the dichroic mirror unit 14 is rotated about the rotation axis RA2, the optical axis of the blue laser light BL reflected by the dichroic mirror 105 turns in a direction parallel to the X-Z plane. Thus, the optical axis of the blue laser light BL entering the condenser lens 107 of the light collecting lens unit 15 turns in a direction parallel to the X-Z plane, and the irradiation position of the blue laser light BL with respect to the flow cell D1 displaces in a direction (X-axis direction) perpendicular to the flow path D15, as shown in FIG. 17D.

At the time of position adjustment of the blue laser light BL, the rotation position of the blue light source unit 13 is adjusted so that the irradiation position of the blue laser light BL separates in the Y-axis direction by a predetermined distance from the irradiation position of the red laser light RL, and furthermore, the rotation position of the dichroic mirror unit 14 is adjusted so that the intensity peak position of the blue laser light BL is positioned at the middle of the flow path D15. Thus, after the position adjustment of the blue light source unit 13 and the dichroic mirror unit 14 is completed, the two nuts 135 are tightened to fix the blue light source unit 13 to the base 11, and furthermore, the two nuts 143 are tightened to fix the dichroic mirror unit 14 to the base 11. The position adjustment of the blue laser light BL is thereby completed.

According to the present configuration example, the blue light source unit 13 and the dichroic mirror unit 14 are independently turned to adjust the irradiation position of the blue laser light BL. The adjustment operation of the irradiation position of the blue laser light BL thus can be simplified. The blue light source unit 13 and the dichroic mirror unit 14 are independently turned, and thus the turning mechanism with respect to each unit can be simplified, and miniaturization and simplification of the light irradiation unit UD can be achieved. Furthermore, the light irradiation unit UD can be made compact since the red light source unit 12, the blue light source unit 13, the dichroic mirror unit 14, and the light collecting lens unit 15 are attached to each surface of the cube-shaped base 11.

In the configuration example described above, the blue light source unit 13 is turned about the rotation axis (rotation axis perpendicular to the flow path D15) RA1 parallel to the Z-axis, and the dichroic mirror unit 14 is turned about the rotation axis (rotation axis parallel to the flow path D15)

RA2 parallel to the Y-axis direction, but the configuration of the light irradiation unit UD is not limited thereto. For example, the blue light source unit 13 may be turned about the rotation axis (rotation axis parallel to the flow path D15) parallel to the Y-axis direction, and the dichroic mirror unit 14 may be turned about the rotation axis (rotation axis perpendicular to the flow path D15) parallel to the Z-axis.

FIG. 18A is a view schematically showing the main configuration of the light irradiation unit UD after the assembly according to the variant.

In the present variant, the step portion 11 is formed on the surface on the negative side of the X-axis of the base 11, and the supporting body 141 is mounted on the step portion 111. The attachment method of the supporting body 141 with respect to the base 11 is similar to the configuration example described above. Thus, the dichroic mirror unit 14 can be turned by a predetermined angle range about the rotation axis RA2 parallel to the X-axis. The blue light source unit 13 is attached to the base 11 so that the rotation axis RA1 becomes parallel to the Y-axis. In this case, the recess 112 is formed to form an inner wall surface in the positive and negative direction of the X-axis, and the supporting body 131 is screw-fastened in the Y-axis direction.

In the variant, when the blue light source unit 13 is turned about the rotation axis RA1, the optical axis of the blue laser light BL entering the dichroic mirror 105 turns in a direction parallel to the X-Z plane. Thus, the optical axis of the blue laser light BL entering the condenser lens 107 of the light collecting lens unit 15 turns in a direction parallel to the X-Z plane, and the irradiation position of the blue laser light BL with respect to the flow cell D1 displaces in a direction (X-axis direction) perpendicular to the flow path D15, as shown in FIG. 18C.

When the dichroic mirror unit 14 is rotated about the rotation axis RA2, the optical axis of the blue laser light BL reflected by the dichroic mirror 105 turns in a direction parallel to the Y-Z plane. The optical axis of the blue laser light BL entering the condenser lens 107 of the light collecting lens unit 15 thus turns in a direction parallel to the Y-Z plane, and the irradiation position of the blue laser light BL with respect to the flow cell D1 displaces in a direction (Y-axis direction) parallel to the flow path D15, as shown in FIG. 18B.

In the variant as well, the blue light source unit 13 and the dichroic mirror unit 14 are independently turned, so that the irradiation position of the blue laser light BL can be adjusted. The effects similar to the configuration example described above may be thereby obtained. In the variant as well, after the position adjustment of the blue light source unit 13 and the dichroic mirror unit 14 is completed, the corresponding nuts are tightened thus fixing the blue light source unit 13 and the dichroic mirror unit 14 to the base 11.

In the configuration example described above and the present variant, the light irradiation optical system D3 is configured so that the red laser light RL is transmitted through the dichroic mirror 105, and the blue laser light BL is reflected by the dichroic mirror 105, but the light irradiation optical system D3 may be configured so that the blue laser light BL is transmitted through the dichroic mirror 105 and the red laser light RL is reflected by the dichroic mirror 105. In this case, the position adjustment of the blue laser light BL is carried out by the position adjustment mechanism PA shown in FIGS. 15A and 15B, and the position adjustment of the red laser light RL is carried out by the turning of the red light source unit 12 and the turning of the dichroic mirror unit 14.

Varian

The embodiment and the analyzing examples of the present invention have been described, but the embodiment of the present invention is not limited thereto.

For example, in the embodiment described above, the blood is assumed as the measurement target, but urine may be the measurement target. In other words, the present invention can be applied to an apparatus for measuring the particles in the biological specimen such as blood, urine, and the like.

In the optical system shown in FIGS. 3A and 3B, the forward light collecting lens 201 is assumed as the achromatic lens, and chromatic aberration is corrected with respect to two wavelengths of the red scattered light RS and the blue scattered light BS. However, the forward light collecting lens 201 may include a normal light collecting lens that does not have the chromatic aberration correcting function. A diffraction lens may be used in place of the achromatic lens.

In this case, the converging positions of the red scattered light RS and the blue scattered light BS are shifted in the Z-axis direction, as schematically shown in FIG. 19A. In the configuration of FIG. 19A, the pin hole 206 for the blue scattered light BS and the pin hole 207 for the red scattered light RS are arranged at the converging position of the blue scattered light BS and the converging position of the red scattered light RS, respectively, and furthermore, the photodiode 208 for the blue scattered light BS and the photodiode 209 for the red scattered light RS are arranged on the positive side of the Z-axis of the pin holes 206, 207, respectively. The blue scattered light BS and the red scattered light RS are guided to the light receiving surfaces 208a, 209a, respectively.

If the shift in the converging positions of the red scattered light RS and the blue scattered light BS is small, one pin hole formed with two holes having different diameters from each other may be used. In this case, the diameter of each hole is set according to the beam diameters of the red scattered light RS and the blue scattered light BS at the arrangement position of the pin hole. If the shift in the converging positions of the red scattered light RS and the blue scattered light BS is small, one photodiode with two light receiving surfaces having different area from each other may be used. In this case, the area of each light receiving surface is set according to the beam sizes of the red scattered light RS and the blue scattered light BS at the arrangement position of each light receiving surface. In this case, the two light receiving surfaces do not necessarily need to be on the same plane, and may be shifted in the Z-axis direction. If the two light receiving surfaces are shifted from each other in the Z-axis direction, the area of the light receiving surfaces does not necessarily need to be different and may be the same area.

Furthermore, in the optical system shown in FIGS. 3A and 3B, the irradiation position EP1 of the blue laser light BL and the irradiation position EP2 of the red laser light RL are shifted in a direction (Y-axis direction) parallel to the flow path D15 by inclining the dichroic mirror 105. However, the dichroic mirror 105 may be arranged such that the center axis (optical axis) of the blue laser light BL and the center axis (optical axis) of the red laser light RL after passing through the dichroic mirror 105 coincide with each other, so that the same irradiation position EP0 on the flow path D15 may be irradiated with the blue laser light BL and the red laser light RL.

In this case, for example, a light dividing element 210 for separating the optical path of the blue scattered light BS and the optical path of the red scattered light RS is arranged in the forward scattered light receiving optical system D4, as schematically shown in FIG. 19B. The light dividing element 210 is a transparent member in which the incident surface and the emit surface are parallel to each other, and is made of a material such as glass, and the like. As shown in FIG. 19B, the optical path of the blue scattered light BS can be shifted toward the negative side of the Y-axis with respect to the optical path of the red scattered light RS by inclining the light dividing element 210 in a direction parallel to the Y-Z plane. Thus, the blue scattered light BS and the red scattered light RS can be guided to the light receiving surfaces 205a, 205b, respectively. A diffraction grating having wavelength selecting property can be used in place of the light dividing element 210 to separate the optical path of the blue scattered light BS and the optical path of the red scattered light RS.

When the same irradiation position EP0 on the flow path D15 is irradiated with the blue laser light BL and the red laser light RL, the dichroic mirror 211 shown in FIG. 19C may be arranged in the forward scattered light receiving optical system D4 in place of the light dividing element 210 shown in FIG. 19B. The dichroic mirror 211 reflects the blue scattered light BS and transmits the red scattered light RS. In this configuration, the pin hole 212 for the blue scattered light BS is arranged at the converging position of the blue scattered light BS, and furthermore, the photodiode 213 for the blue scattered light BS is arranged at the post stage thereof. The pin hole 214 for the red scattered light RS is arranged at the converging position of the red scattered light RS, and furthermore, the photodiode 215 for the red scattered light RS is arranged at the post stage thereof. Thus, the blue scattered light BS and the red scattered light RS can be guided to the light receiving surfaces 213a, 215a, respectively.

In the configuration example shown in FIGS. 19A to 19C as well, the light irradiation unit UD shown in FIG. 13 to FIGS. 18A to 18C can be used.

In the embodiment of the present invention, the irradiation positions of the plurality of light sources are adjusted to shift using the light irradiation unit UD shown in FIG. 13 to FIGS. 18A to 18C, and the forward scattered light generated by the respective light source is acquired, but this is not the sole case. For example, even when acquiring the fluorescence signal by different light sources, the irradiation position can be easily adjusted using the light irradiation unit UD if there is a need to shift the irradiation positions of the light sources.

In the optical system shown in FIGS. 3A and 3B, the semiconductor laser 101 that emits the red laser light RL and the semiconductor laser 103 that emits the blue laser light BL are individually arranged, but for example, the semiconductor laser 101 may be configured to include two light emitting portions (light sources), and emit the red laser light RL and the blue laser light BL in the Z-axis direction from each light emitting portion. In this case, the semiconductor laser 103, the collimator lens 104, and the dichroic mirror 105 are omitted from the optical system shown in FIGS. 3A and 3B. The collimator lens 102 has a chromatic aberration correcting function with respect to the wavelength of the red laser light RL and the wavelength of the blue laser light BL. Furthermore, the two light emitting portions are arranged in the semiconductor laser 101 so as to shift in the Y-axis direction.

In this case, the interval of the irradiation positions EP1 and EP2 of the blue laser light BL and the red laser light RL on the flow path D15 is determined by the interval of the two light emitting portions and the magnification of the light irradiation optical system D3. Therefore, the interval of the two light emitting portions arranged in the semiconductor laser 103 is set such that the interval of the irradiation positions EP1 and E2 becomes a desired value.

Furthermore, in the optical detector D according to the embodiment described above, the blood cells are classified using the forward scattered light (red scattered light RS, blue scattered light BS) of the light of each wavelength emitted toward the front side (positive direction of Z-axis) from the flow cell D1. However, this is not the sole cases, and the blood cells may be classified using the side scattered light of the light of each wavelength emitted toward the side (positive direction of X-axis) from the flow cell D1.

The wavelength of the two lights irradiated on the flow cell D1 is also not limited to the wavelength described above, and the wavelength may be appropriately selected so that the absorption coefficient of hemoglobin differs. For example, a yellow laser light (emission wavelength 550 to 600 nm) having high absorption degree of the red blood cells similar to the blue laser light BL may be used in place of the blue laser light BL. Furthermore, other wavelengths may be used as long as the properties of the scattered light differ for every blood cell. However, the distribution of each blood cell can be more clearly sectionalized and each blood cell can be counted as described above, by setting the wavelength of the blue laser light BL to the wavelength described in the above embodiment.

In the first analyzing example, the threshold value V1 is set only with respect to the intensity of the red scattered light RS, and the acquisition of the forward scattered light data is limited, but a threshold value may also be set with respect to the intensity of the blue scattered light BS and the acquisition of the forward scattered light data may be limited. In the second analyzing example, the threshold value V2 is set only with respect to the intensity of the blue scattered light BS and the acquisition of the forward scattered light data is limited, but a threshold value may also be set with respect to the intensity of the red scattered light RS and the acquisition of the forward scattered light data may be limited.

In the first to third analyzing examples, the scattergram is displayed on the display section 41, but the scattergram does not necessarily need to be displayed. However, the evaluation of the analysis result can be smoothly carried out when the scattergram is displayed since the separation extent of each blood cell can be visually checked.

In the embodiment described above, the blood cell analyzer 1 is configured to be able to measure not only the measurement specimen in which the first reagent and the second reagent are not mixed but also the measurement specimen in which such reagents are mixed. However, the blood cell analyzer 1 does not necessarily need to have a configuration for processing the measurement specimen in which the first reagent and the second reagent are mixed, and for example, the blood cell analyzer 1 may be configured to be able to measure only the measurement specimen in which the first reagent and the second reagent are not mixed according to the first to third analyzing examples. In this case, the container 251 containing the first reagent and the container 252 containing the second reagent are omitted from the measurement unit 2 shown in FIG. 2. The fluorescence light receiving optical system D6 is omitted from the optical detector D shown in FIG. 3A, and the dichroic mirror D52 is changed to a total reflection mirror. Accordingly, the configuration of the blood cell analyzer 1 can be simplified. Since the containers 251 and 252 are omitted, the trouble of connecting the containers 251 and 252 to the specimen preparing section 25 is omitted, and the cost can be reduced.

In addition, the embodiment of the present invention may be appropriately modified within a scope of the technical concept defined in the Claims.

The invention claimed is:

1. A particle measuring apparatus comprising:
a flow cell configured to flow a specimen;
a first light source configured to emit light having a first wavelength;
a second light source configured to emit light having a second wavelength different from the first wavelength;
an irradiation optical system configured to irradiate the flow cell with light emitted from the first light source and the second light source,
the irradiation optical system including:
a dichroic mirror configured to transmit the light emitted from the first light source and reflect the light emitted from the second light source, and
a light collecting lens configured to collect the light emitted from the first and second light sources and passed through the dichroic mirror at the flow cell,
wherein the second light source and the dichroic mirror are turnable about rotation axis that are orthogonal to one another.

2. The particle measuring apparatus according to claim 1, wherein the dichroic mirror and the light collecting lens of the irradiation optical system are configured to guide light having the first wavelength emitted from the first light source to a first irradiation position in the flow cell, and to guide light having the second wavelength emitted from the second light source to a second irradiation position different from the first irradiation position in the flow cell.

3. The particle measuring apparatus according to claim 2, wherein the dichroic mirror and the light collecting lens of the irradiation optical system are adjustable so as to irradiate the same position in the flow cell with light having the first wavelength emitted from the first light source and light having the second wavelength emitted from the second light source; and
the light receiving optical system includes a light dividing section configured to separate an optical path of the scattered light based on the light having the first wavelength and an optical path of the scattered light based on the light having the second wavelength.

4. The particle measuring apparatus according to claim 2, wherein the first irradiation position and the second irradiation position are spaced apart from one another in a flow direction of a specimen in the flow cell.

5. The particle measuring apparatus according to claim 3, further comprising:
an analyzing section configured to acquire first scattered light data based on the scattered light received by the first light receiving portion and second scattered light data based on the scattered light received by the second light receiving portion, respectively; wherein
the analyzing section configured to associate the first scattered light data with the second scattered light data obtained from the same measurement particle to each other, and execute analysis based on the first scattered light data and the second scattered light data.

6. The particle measuring apparatus according to claim 1, wherein an absorption coefficient of hemoglobin of the first wavelength is different from an absorption coefficient of hemoglobin of the second wavelength.

7. The particle measuring apparatus according to claim 1, further comprising a base attached with the first light source, the second light source and the irradiation optical system;
wherein the second light source is turnably attached to the base;
the dichroic mirror is attached to the base so as to be turnable about the rotation axis orthogonal to the rotation axis of the second light source; and
a light collecting position of the light emitted from the second light source is displaced in either one direction of a first direction that is parallel to the flow path of the flow cell and a second direction that traverses the flow path when the second light source is turned with respect to the base, and the light collecting position of the light emitted from the second light source is displaced in the other direction of the first and second directions when the dichroic mirror is turned with respect to the base.

8. The particle measuring apparatus according to claim 7, wherein the second light source is attached to the base so as to be turnable about an axis perpendicular to the flow path of the flow cell, and the dichroic mirror is attached to the base so as to be turnable about an axis parallel to the flow path of the flow cell.

9. The particle measuring apparatus according to claim 7, wherein the second light source is attached to the base so as to be turnable about an axis parallel to the flow path of the flow cell, and the dichroic mirror is attached to the base so as to be turnable about an axis perpendicular to the flow path of the flow cell.

10. The particle measuring apparatus according to claim 7, wherein the irradiation optical system further comprises a collimator lens between the second light source and the dichroic mirror, and the second light source and the collimator lens both turnably attached to the base.

11. The particle measuring apparatus according to claim 7, further comprising: a position adjustment mechanism configured to support the base so as to be displaceable in a direction of approaching the flow path of the flow cell and a direction of traversing the flow path.

12. The particle measuring apparatus according to claim 7, wherein the first light source and the light collecting lens are fixed to the base.

13. The particle measuring apparatus according to claim 1, further comprising:
a first light receiving portion configured to receive light obtained by irradiating a measurement particle passing through the flow cell with light from the first light source; and
a second light receiving portion configured to receive light obtained by irradiating a measurement particle passing through the flow cell with light from the second light source.

14. The particle measuring apparatus according to claim 13, further comprising: a light receiving optical system including a chromatic aberration correction lens configured to guide light generated by irradiating a measurement particle with light having the first wavelength to the first light receiving portion, and to guide light generated by irradiating a measurement particle with light having the second wavelength to the second light receiving portion.

15. The particle measuring apparatus according to claim 13, wherein the first light receiving portion and the second light receiving portion are adjacent to each other in a direction parallel to light receiving surfaces of the first light receiving portion and the second light receiving portion.

16. The particle measuring apparatus according to claim 13, wherein the first light receiving portion and the second light receiving portion are both arranged in a housing of an optical detector.

17. The particle measuring apparatus according to claim 13, wherein the light receiving surfaces of the first light receiving portion and the second light receiving portion are such that their positions in a direction perpendicular to the light receiving surfaces of the light receiving portions are parallel with respect to each other.

18. The particle measuring apparatus according to claim 13 further comprising: a light receiving optical system including a chromatic aberration correcting lens configured to collect the scattered light generated from the measurement particle passing through the first irradiation position at the first light receiving portion, and collect the scattered light generated from the measurement particle passing through the second irradiation position at the second light receiving portion.

* * * * *